(12) United States Patent
Moberg et al.

(10) Patent No.: US 8,317,759 B2
(45) Date of Patent: Nov. 27, 2012

(54) MULTI-POSITION INFUSION SET DEVICE AND PROCESS

(75) Inventors: Sheldon B. Moberg, Thousand Oaks, CA (US); Mark Holt, Moorpark, CA (US); Albert D. Candioty, Agoura Hills, CA (US); Julian D. Kavazov, Arcadia, CA (US); Lance E. Shetler, Downey, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 459 days.

(21) Appl. No.: 12/360,813

(22) Filed: Jan. 27, 2009

(65) Prior Publication Data

US 2009/0163878 A1    Jun. 25, 2009

Related U.S. Application Data

(60) Division of application No. 11/004,594, filed on Dec. 3, 2004, now Pat. No. 7,494,481, and a continuation-in-part of application No. 10/705,686, filed on Nov. 10, 2003, now Pat. No. 7,520,867.

(51) Int. Cl.
*A61M 5/00* (2006.01)
(52) U.S. Cl. .............. 604/263; 604/164.01; 604/164.08; 604/174
(58) Field of Classification Search ............... 604/93.01, 604/164.01, 164.04, 164.07, 164.08, 164.1, 604/164.11, 174, 180, 263
See application file for complete search history.

(56) References Cited

U.S. PATENT DOCUMENTS

| | | | |
|---|---|---|---|
| 4,601,708 | A | 7/1986 | Jordan |
| 4,645,495 | A | 2/1987 | Vaillancourt |
| 4,685,903 | A | 8/1987 | Cable et al. |
| 4,743,231 | A | 5/1988 | Kay et al. |
| 4,755,173 | A | 7/1988 | Konopka et al. |
| 4,787,891 | A | 11/1988 | Levin et al. |
| 4,813,939 | A | 3/1989 | Marcus |

(Continued)

FOREIGN PATENT DOCUMENTS

EP    1 421 968 A2    5/2004

OTHER PUBLICATIONS

PCT International Search Report/Written Opinion dated Apr. 13, 2006 for related PCT application PCT/US2005/041006.

(Continued)

*Primary Examiner* — Theodore Stigell
(74) *Attorney, Agent, or Firm* — Foley & Lardner LLP

(57) ABSTRACT

An infusion set for subcutaneous delivery of an infusant. The infusion set may include a base removably attachable to an infusion site and a connector temporarily lockable to the base. The connector can engage the base in a plurality of orientations. The connector locks into the base after at least partial rotation of the connector about the base. The connector may include flexible arms which unlock the connector from the base. The base includes a cannula for insertion through the infusion site. The connector includes a tubing for passing the infusant. The infusant is subcutaneously passable from the tubing through the cannula when the connector is attached to the base. The infusion set may also include a hub removably attachable to the base that includes a needle that extends through the base and the cannula and a guard removably attachable to the base opposite the hub for surrounding the needle.

20 Claims, 20 Drawing Sheets

U.S. PATENT DOCUMENTS

| | | | |
|---|---|---|---|
| 4,955,861 A | 9/1990 | Enegren et al. | |
| 4,966,589 A | 10/1990 | Kaufman | |
| 4,988,339 A | 1/1991 | Vadher | |
| 4,994,042 A | 2/1991 | Vadher | |
| 5,122,119 A | 6/1992 | Lucas | |
| 5,147,375 A | 9/1992 | Sullivan et al. | |
| 5,176,662 A | 1/1993 | Bartholomew et al. | |
| 5,257,980 A | 11/1993 | Van Antwerp et al. | |
| 5,368,045 A | 11/1994 | Clement et al. | |
| 5,390,671 A | 2/1995 | Lord et al. | |
| 5,522,803 A | 6/1996 | Teissen-Simony | |
| 5,533,974 A * | 7/1996 | Gaba | 604/110 |
| 5,545,143 A * | 8/1996 | Fischell | 604/180 |
| 5,545,152 A | 8/1996 | Funderburk et al. | |
| 5,552,803 A | 9/1996 | Rhodes et al. | |
| 5,562,631 A | 10/1996 | Bogert | |
| 5,568,806 A | 10/1996 | Cheney, II et al. | |
| 5,584,813 A | 12/1996 | Livingston et al. | |
| 5,586,553 A | 12/1996 | Halili et al. | |
| 5,591,188 A | 1/1997 | Waisman | |
| 5,607,407 A | 3/1997 | Tolkoff et al. | |
| 5,779,665 A | 7/1998 | Mastrototaro et al. | |
| 5,851,197 A | 12/1998 | Marano et al. | |
| 5,868,711 A | 2/1999 | Kramer et al. | |
| 5,957,895 A | 9/1999 | Sage et al. | |
| 5,968,011 A | 10/1999 | Larsen et al. | |
| 5,980,506 A | 11/1999 | Mathiasen | |
| 6,017,328 A | 1/2000 | Fischell et al. | |
| 6,056,718 A * | 5/2000 | Funderburk et al. | 604/93.01 |
| 6,086,575 A * | 7/2000 | Mejslov | 604/533 |
| 6,093,172 A | 7/2000 | Funderburk et al. | |
| 6,123,690 A | 9/2000 | Mejslov | |
| 6,290,677 B1 | 9/2001 | Arai et al. | |
| 6,293,925 B1 | 9/2001 | Safabash et al. | |
| 6,302,866 B1 | 10/2001 | Marggi | |
| 6,355,021 B1 | 3/2002 | Nielsen et al. | |
| 6,461,329 B1 | 10/2002 | Van Antwerp et al. | |
| 6,572,586 B1 | 6/2003 | Wojcik | |
| 6,579,265 B1 | 6/2003 | Kihara et al. | |
| 6,579,267 B2 | 6/2003 | Lynch et al. | |
| 6,685,674 B2 | 2/2004 | Douglas et al. | |
| 6,736,797 B1 | 5/2004 | Larsen et al. | |
| 6,923,791 B2 | 8/2005 | Douglas | |
| 7,115,114 B2 * | 10/2006 | Caizza | 604/240 |
| 7,494,481 B2 * | 2/2009 | Moberg et al. | 604/174 |
| 7,520,867 B2 * | 4/2009 | Bowman et al. | 604/93.01 |
| 2002/0022855 A1 | 2/2002 | Bobroff et al. | |
| 2002/0072720 A1 | 6/2002 | Hague et al. | |
| 2002/0119711 A1 | 8/2002 | Van Antwerp et al. | |
| 2004/0138620 A1 | 7/2004 | Douglas et al. | |
| 2004/0260235 A1 | 12/2004 | Douglas | |
| 2005/0020972 A1 | 1/2005 | Horisberger et al. | |
| 2005/0101910 A1 | 5/2005 | Bowman et al. | |
| 2005/0101933 A1 | 5/2005 | Marrs et al. | |
| 2005/0107746 A1 | 5/2005 | Pajunk et al. | |
| 2005/0113761 A1 | 5/2005 | Faust et al. | |
| 2006/0211990 A1 * | 9/2006 | Fangrow, Jr. | 604/157 |

OTHER PUBLICATIONS

Notice of Allowance dated Dec. 18, 2008 from related U.S. Appl. No. 10/705,686.
Office Action dated Apr. 30, 2008 in related U.S. Appl. No. 11/004,594.
Office Action dated Apr. 30, 2008 from related U.S. Appl. No. 10/705,686.
Office Action dated Feb. 5, 2007 from related U.S. Appl. No. 11/004,594.
Office Action dated Jun. 1, 2007 from related U.S. Appl. No. 10/705,686.
Office Action dated Jun. 30, 2005 from related U.S. Appl. No. 10/705,686.
Office Action dated Mar. 23, 2006 from related U.S. Appl. No. 10/705,686.
Office Action dated Nov. 13, 2007 from related U.S. Appl. No. 10/705,686.
Office Action dated Nov. 2, 2007 from related U.S. Appl. No. 11/004,594.
Office Action dated Nov. 30, 2005 from related U.S. Appl. No. 10/705,686.
Office Action dated Oct. 11, 2006 from related U.S. Appl. No. 10/705,686.
Office Action dated Sep. 7, 2006 from related U.S. Appl. No. 11/004,594.
US Notice of Allowance dated Oct. 20, 2008 in related U.S. Appl. No. 11/004,594.

* cited by examiner

MULTI-POSITION INFUSION SET DEVICE AND PROCESS

CROSS-REFERENCE TO RELATED PATENT APPLICATIONS

This application is a divisional of U.S. application Ser. No. 11/004,594, filed Dec. 3, 2004, entitled "Multi-Position Infusion Set Device and Process," herein incorporated by reference in its entirety and is a basis for priority. This application is also a continuation-in-part of U.S. application Ser. No. 10/705,686, filed Nov. 10, 2003, entitled "Subcutaneous Infusion Set," herein incorporated by reference in its entirety and is a basis for priority.

BACKGROUND

1. Field of the Invention

The present invention relates to infusion sets and, in particular, to infusion sets having a cannula which is inserted into the skin of a patient to facilitate the subcutaneous transfer of an infusant.

2. Description of Related Art

Infusion sets are typically used for delivering a fluid, drug or other infusant to a subcutaneous location in a patient. While most infusion sets include a delivery tube connected to an infusion pump or other fluid or drug delivering device, the configuration of some infusion sets have been disadvantageous to patients for a variety of reasons.

If an infusion set includes a base portion disposed on the skin of a patient and a connector portion that attaches to the base portion, a delivery tube may be attached to the connector portion. Thus, when the connector portion is attached to the base portion, the delivery tube may be connected to an infusion pump or other device for fluid delivery, permitting the patient to administer the desired or necessary infusant. However, if the connector portion of the infusion set is positioned in such a manner that the delivery tube is in a position that is undesirable or impractical for the patient, the patient is resigned to removing the base portion from the patient's skin and inserting a new infusion set base, since the old one cannot be safely reused. It is not normally possible to re-orient the base portion because re-orienting the base portion typically includes re-inserting a needle into the skin. Also, re-orienting the base portion can be discomforting, painful or could lead to infection and thus is undesirable for the patient.

Some infusion sets are configured so that the connector portion and, thus, the delivery tube, may rotate freely about the base portion. Freely rotating infusion sets have disadvantages. Generally, too much movement of the delivery tube is undesirable. For example, because the delivery tube is typically delivering a fluid or some type of drug or infusant to a patient, it is necessary that the fluid path remain unobstructed. If the delivery tube is permitted to rotate freely around the base portion of the infusion set, the delivery tube may be subject to entanglement, twisting, kinking or the like, interrupting the infusion process. In addition, a freely rotating delivery tube can, at times, appear or feel to the patient to be disconnected from the patient and, thus, may result in a sense of insecurity for the patient.

The needs of patients who rely on infusion sets are numerous. For example, patients need infusion sets that require a positive action for releasing a connector from a base—infusion sets that release inadvertently are inconvenient and worrisome. In addition, while it is desirable that the size of the infusion set be minimized, it is also desirable that a patient be able to hold on to the infusion set and that protective pieces of the infusion set remain in place when the infusion set is in storage. Moreover, patients desire the flexibility to attach a connector to a base in multiple positions but also a connector that maintains the position of a delivery tube so that the aforementioned problems of a freely rotating tube are avoided.

SUMMARY OF THE DISCLOSURE

According to an embodiment of the present invention, an infusion set may include a base removably attachable to an infusion site for providing a subcutaneous path for an infusant and a connector temporarily lockable to the base. The base may be engagable by the connector in a plurality of orientations. In addition, the base may include a plurality of apertures and the connector may include a plurality of tabs insertable into the plurality of apertures.

The connector may be at least partially rotatable about the base and at least one tab of the plurality of tabs may be rotatable from a position within at least one aperture of the plurality of apertures to a locked position. The base may include at least one abutment for locking at least one tab of the plurality of tabs into a position. The connector may include a plurality of arms and each arm of the plurality of arms may be fixedly attached to a tab of the plurality of tabs. The plurality of arms may be flexible. Each arm of the plurality of arms may be flexed to remove a tab of the plurality of tabs from a locked position to an unlocked position. The connector may be removable from the base by simultaneously flexing the plurality of arms.

According to an embodiment of the present invention, the base may include a cannula for insertion through the infusion site. The connector may include a tubing for passing the infusant. The infusant may be subcutaneously passable from the tubing through the cannula when the connector is attached to the base.

Embodiments of the invention may include a hub removably attachable to the base. The hub may include a needle extending through the base and through the cannula. Embodiments of the invention may also include a guard removably attachable to the base opposite the hub for surrounding the needle. The needle may be subcutaneously insertable into the infusion site for subcutaneously positioning the cannula.

The base may include an adhesive pad for attaching to the infusion site. The infusion site may be the skin of a patient.

According to an embodiment of the present invention, a method for delivering an infusant may include positioning a base at an infusion site for providing a subcutaneous path for the infusant; engaging the base with a connector, the connector being temporarily lockable to the base; and rotating, at least partially, the connector about the base until the connector temporarily locks to the base. The base may be engagable by the connector in a plurality of orientations. The base may include a plurality of apertures and the connector may include a plurality of tabs. The method may further include inserting the plurality of tabs into the plurality of apertures. The method may further include providing at least one abutment on the base for locking at least one tab of the plurality of tabs in the locked position and may further include providing a plurality of arms on the connector. Each arm of the plurality of arms may be fixedly attached to a tab of the plurality of tabs. The plurality of arms may be flexible and the method may further include flexing each arm of the plurality of arms to remove a tab of the plurality of tabs from a locked position to an unlocked position. The method may further include simultaneously flexing the plurality of arms to remove the connector from the base and inserting a cannula connected to the base through the infusion site.

The method may further include providing a hub removably attachable to the base, the hub including a needle extending through the base and through the cannula; providing a guard removably attachable to the base opposite the hub for surrounding the needle; and subcutaneously inserting the needle into the infusion site for subcutaneously positioning the cannula.

According to an embodiment of the present invention, an infusion set may include a base removably attachable to an infusion site for providing a subcutaneous path for an infusant; a connector removably attachable to the base; and a locking mechanism for temporarily locking the connector to the base. The base may be engagable by the connector in a plurality of orientations. The base may include a plurality of apertures.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

In the following description of preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the preferred embodiments of the present invention.

Embodiments of the present invention relate to infusions sets and processes of using and making same. Such infusion sets may be employed to transfer a medication, an infusant and the like between a reservoir and a patient. For example, an infusion set may be used by connecting the infusion set to an insulin infusion pump to a diabetic patient. Other embodiments may be employed for other medical or infusion applications or procedures.

Figure 1:
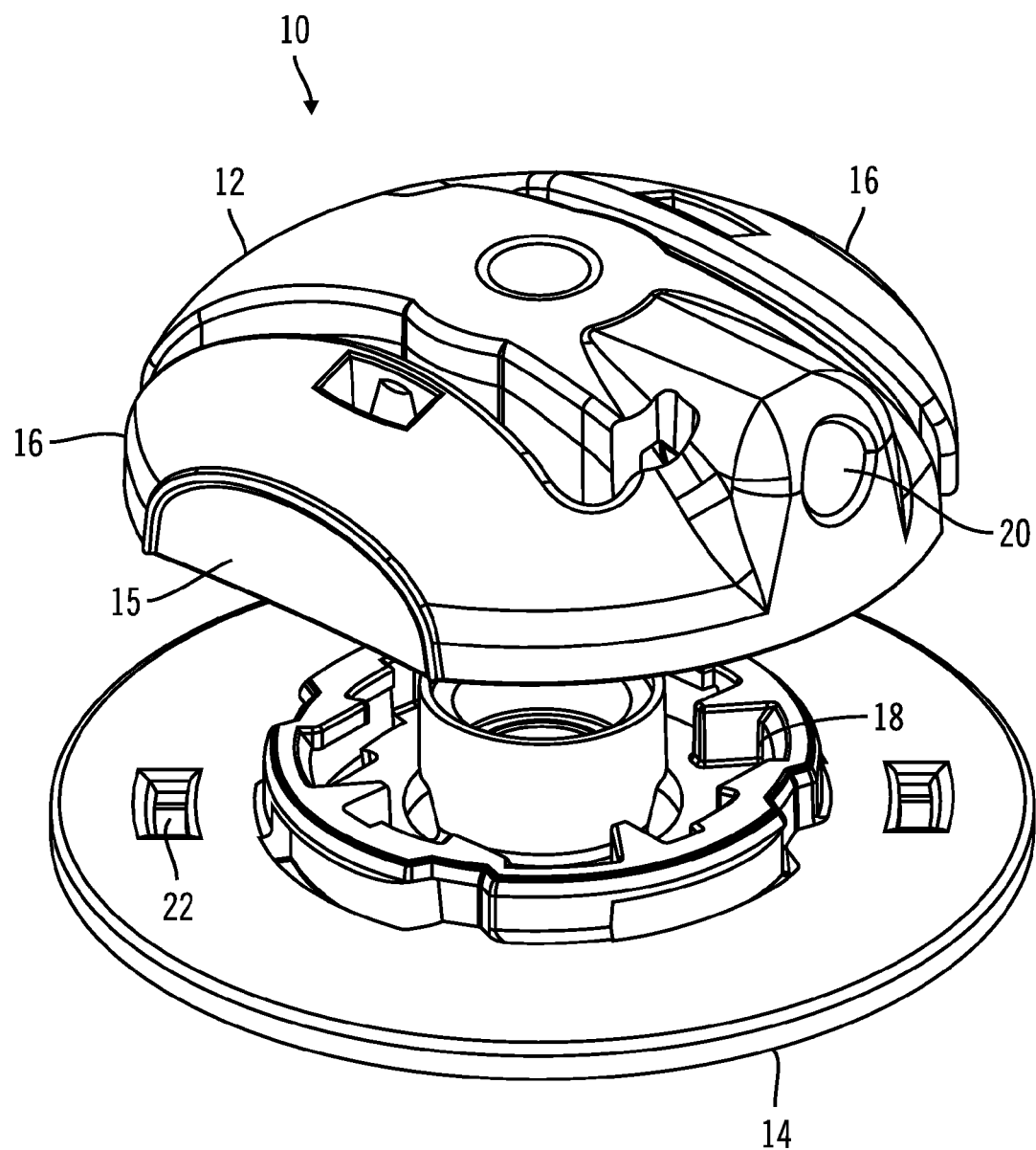
FIG. 1 shows a perspective view of an infusion set according to an embodiment of the present invention.

FIG. 1 shows an infusion set 10 according to an embodiment of the present invention. The embodiment of the infusion set 10 shown in FIG. 1 includes, but is not limited to, a connector 12 and a base 14. The connector 12 and the base 14 in the embodiment of the invention shown in FIG. 1 are configured such that the connector 12 is removably attachable to the base 14.

The connector 12 may include, without limitation, two or more arms 16 that may be used to facilitate connecting and/or removing the connector 12 to the base 14. In addition, the arms 16 may include a cutout, depression or surface 15 that may aid a user or patient in gripping the connector 12. The connector 12 may also include a port 20 to which is connected a tubing (not shown) for passing a fluid, medication or other infusant from an infusion pump, reservoir or the like through the infusion set to a subcutaneous location in a patient.

The base 14 may include a plurality of grooves, cutouts, depressions, spacings, apertures and the like to facilitate a connection between the connector 12 and the base 14 as will be explained in greater detail below. For example, as can be seen in the embodiment of the invention shown in FIG. 1, the base 14 includes an inner depression 18 for accepting a tab or other extended member disposed on the connector 12 as well as an aperture 22 for accepting a tab or other extended member disposed on a hub, as will be explained in greater detail below.

In the embodiment of the invention shown in FIG. 1, the connector 12 and the base 14 are of a substantially circular disc shape. However, the connector 12 and the base 14 need not be circular and could be designed to be any shape convenient to or desired by a patient, healthcare professional or other user of the infusion set. In addition, the connector 12 and the base 14 may be designed in a variety of sizes. For example, according to an embodiment of the present invention, the connector 12 and the base 14 may be designed small enough to be unobtrusive to a patient when wearing the infusion set 10 but large enough so that the patient can easily hold onto the infusion set 10 when applying the infusion set 10 to or removing the infusion set 10 from the patient's skin. For example, the connector and base may have a circular disc shape with a diameter in the range of about 0.5 inches (1.27 cm.) to about 1.25 inches (3.175 cm.).

Also, according to an embodiment of the present invention, the base 14 may be designed so that it can be affixed to a patient's skin. For example, the base 14 may include an adhesive applied to a bottom portion of the base 14, i.e., the portion of the base 14 that comes into contact with a patient's skin, so that the base 14 adheres to the patient's skin when applied. According to another embodiment of the present invention, the base 14 may be supplied with an adhesive pad attached to a portion of the base 14, such as a bottom portion, for example, which may adhere to the patient's skin when applied.

Figure 2:
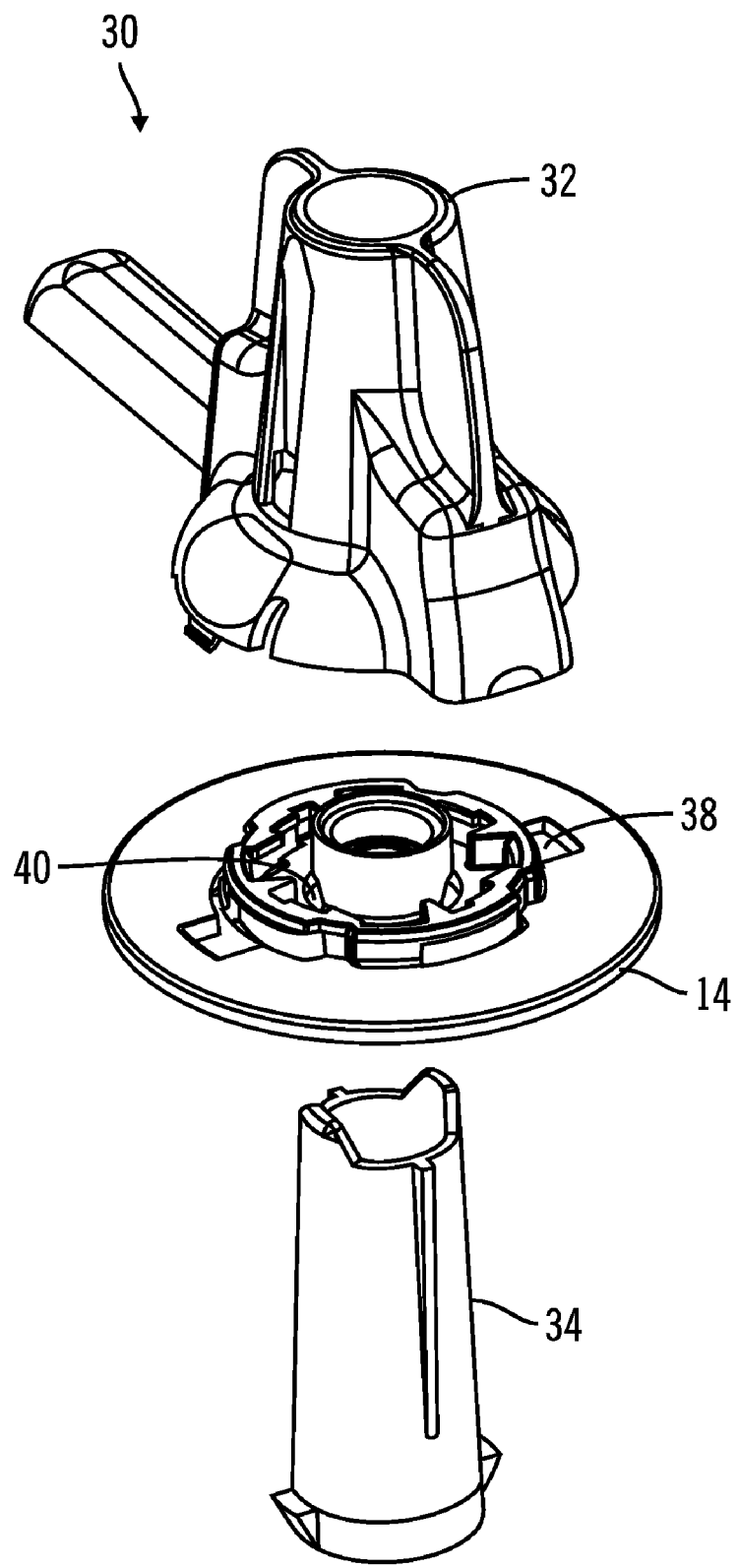
FIG. 2 shows a perspective view of an infusion set according to another embodiment of the present invention.

FIG. 2 shows an infusion set 30 according to another embodiment of the present invention. The infusion set 30 shown in FIG. 2 includes, without limitation, a hub 32, a base 14 and a guard 34. Whereas the embodiment of the infusion set shown in FIG. 1 may be used during operation with a patient, the embodiment of the invention shown in FIG. 2 may be used during storage. As will be explained in greater detail below, the hub 32 affixes to a top or first side of the base 14 via a hub aperture 38. In addition, the guard 34 attaches to a bottom or second side of the base 14 via the guard apertures 40. The hub 32 may be used to cover the base 14 and to facilitate application of the base 14 onto the skin of a patient. The guard 34 may be used as a protective element to cover a needle (not shown) or other protrusion that may extend through the bottom of the base 14.

According to an embodiment of the present invention, the base 14 may be designed in a variety of ways. For example, the base 14 may be designed with sufficient size and shape so that it is manageable, for example, easy to grip and maneuver, for a patient or other user when applying the base 14 to a patient's skin. According to an embodiment of the present invention, the base 14 may be designed large enough so that a patient may secure the base 14 with his or her fingers when removing the hub 32 from the base 14.

The embodiments of the infusion sets shown in FIGS. 1 and 2 may be made from a variety of materials. For example, according to embodiments of the present invention, the connector 12, base 14, hub 32 and guard 34 of the infusions sets shown in FIGS. 1 and 2 may be made from plastics, such as PVC, polypropylene, polycarbonate and the like, for example, suitable rubbers, polymers, other synthetic materials and the like or combinations of two or more of these materials used together on a single part utilizing processes such as over molding or two-shot molding.

Figure 3:
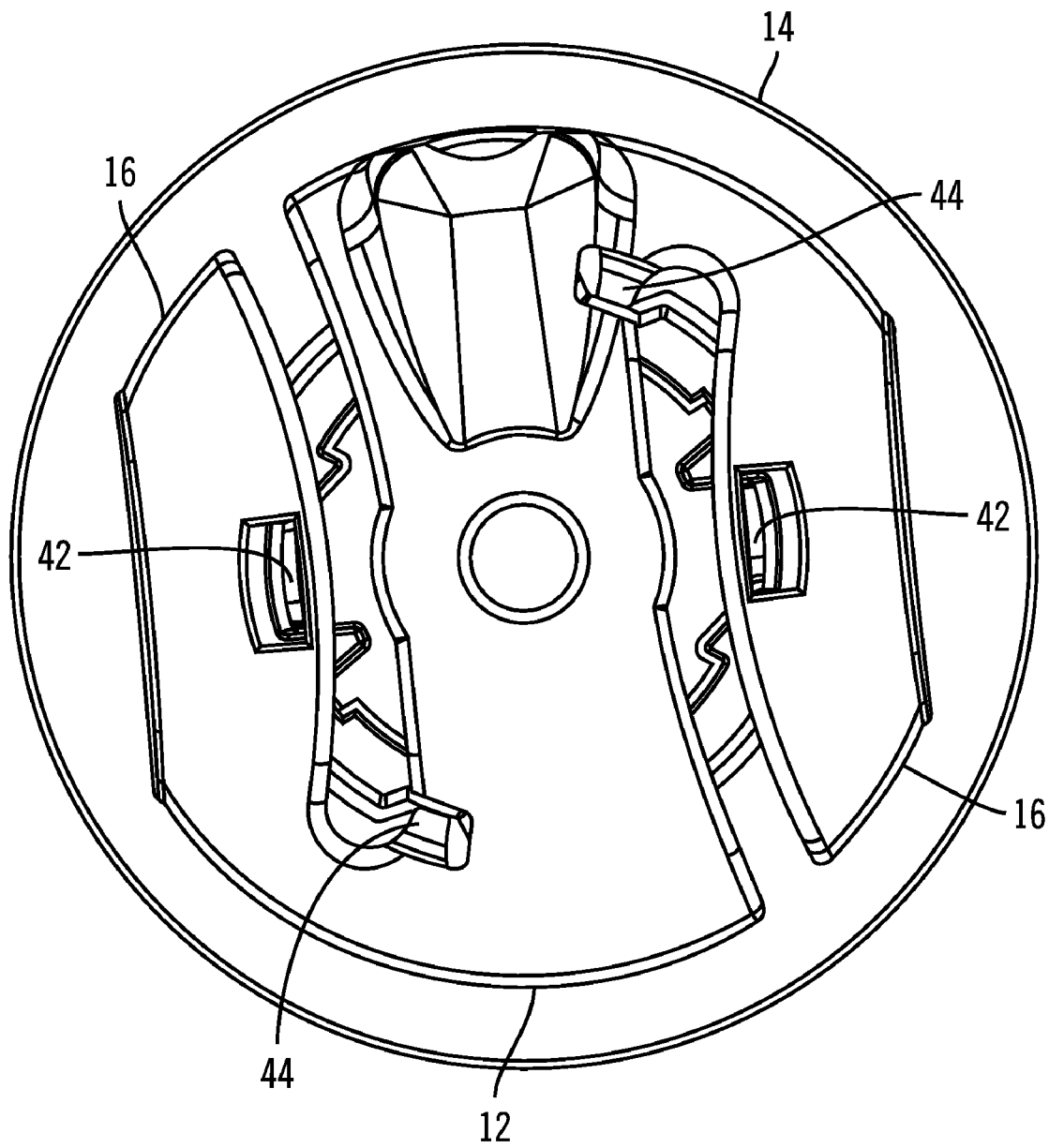
FIG. 3 shows a top-down view of a connector in an unlocked position on a base according to an embodiment of the present invention.

FIG. 3 shows a top down view of the connector 12 as it rests in an unlocked position on the base 14 according to an embodiment of the present invention. As can be seen in the embodiment of the invention shown in FIG. 3, the illustrated connector 12 includes inner tabs 42 fixedly attached or otherwise extending in a cantilevered fashion from the arms 16. Outer tabs 44 extend, in a cantilevered fashion, from a portion of the connector 12 where the arms 16 extend from the body of the connector 12. The inner tabs 42 and the outer tabs 44 are used to align the connector 12 with the base 44 and lock the connector 12 into place, thereby maintaining the position of the connector 12 with respect to the base 14 as will be explained in greater detail below.

Figure 4:
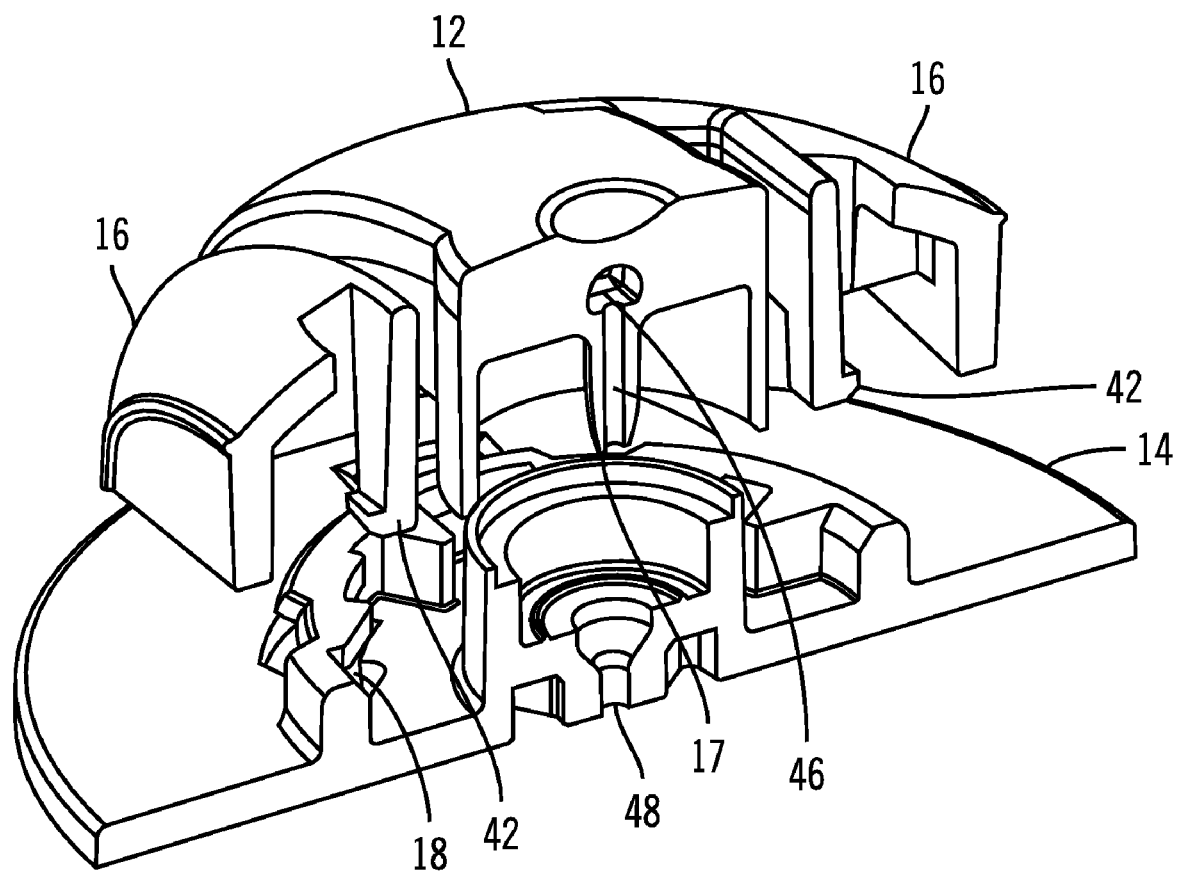
FIG. 4 shows a perspective cutaway view of a connector and a base according to an embodiment of the present invention.

FIG. 4 shows a prospective cutaway view of the connector 12 and the base 14 according to an embodiment of the present invention. As shown in FIG. 4, the inner tabs 42 extend away from the arms 16. When the connector 12 engages the base 14, an inner tab 42 on the connector 12 may be positioned in an inner depression 18 in the base 14. The depression 18 may be sized liberally, for example, larger than the size of the inner tab 42, so that the inner tab 42 may be easily positioned within it without having to depress the arms 16 on the connector 12.

Also shown in FIG. 4 is a connector duct 46 in a centrally located projection 17 of the connector 12 and a base duct 48 in the base 14. The base duct 48 has a flared or enlarged diameter open-facing toward the connector 12. The connector duct 46 is contiguous with the port 20 (not shown in FIG. 4) and, thus, will pass a fluid, medicant or other infusant when the infusant passes through a tubing into the port 20. When the connector 12 is engaged with the base 14, the connector duct 46 in the projection 17 of the connector 12 extends at least partially into the enlarged or flared end of the base duct 48 to interface with the base duct 48 such that fluid may pass from the connector 12 to and through the base 14. A subcutaneous cannula or catheter (not shown in FIG. 4) may be affixed to the base duct 48 for passing the fluid into the body of a patient.

Figure 5:
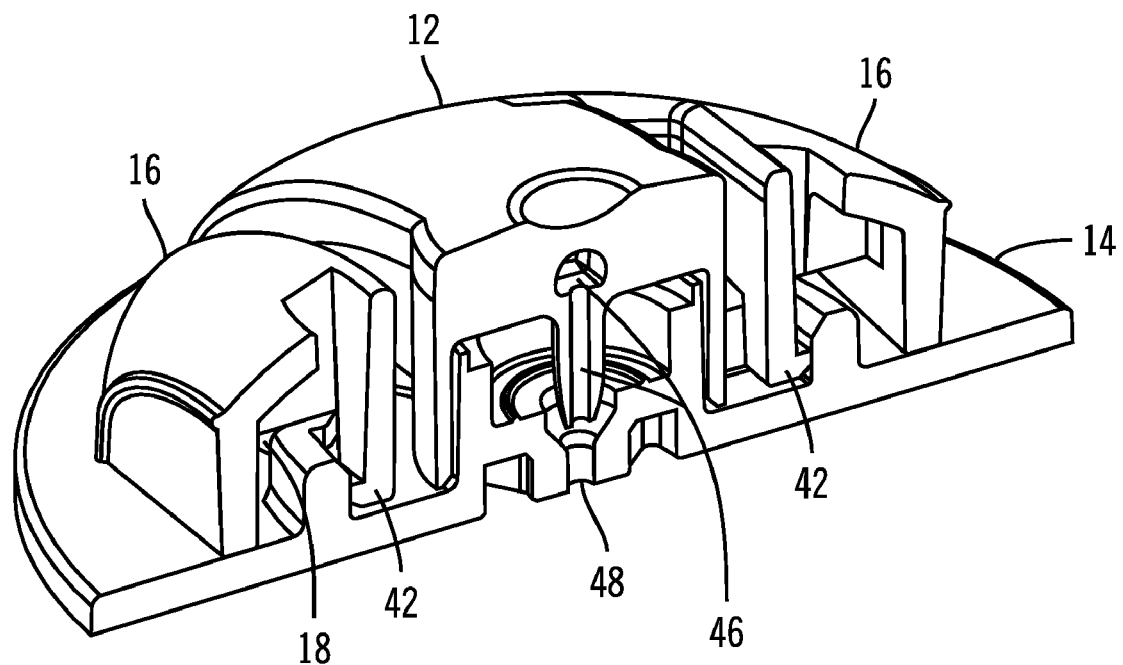
FIG. 5 shows a perspective cutaway view of a connector as it engages a base according to an embodiment of the present invention.

FIG. 5 shows a prospective cutaway view of the connector 12 and the base 14 when the connector 12 is engaged to the base 14 according to an embodiment of the present invention. In FIG. 5, the inner tabs 42 can be seen extending away from the arms 16 and positioned in the depression 18. Moreover, the connector duct 46 can be seen engaging the base duct 48. In FIG. 5, the connector 12 has not been locked onto the base 14 and, thus may be freely removable from the base 14.

Figure 6:
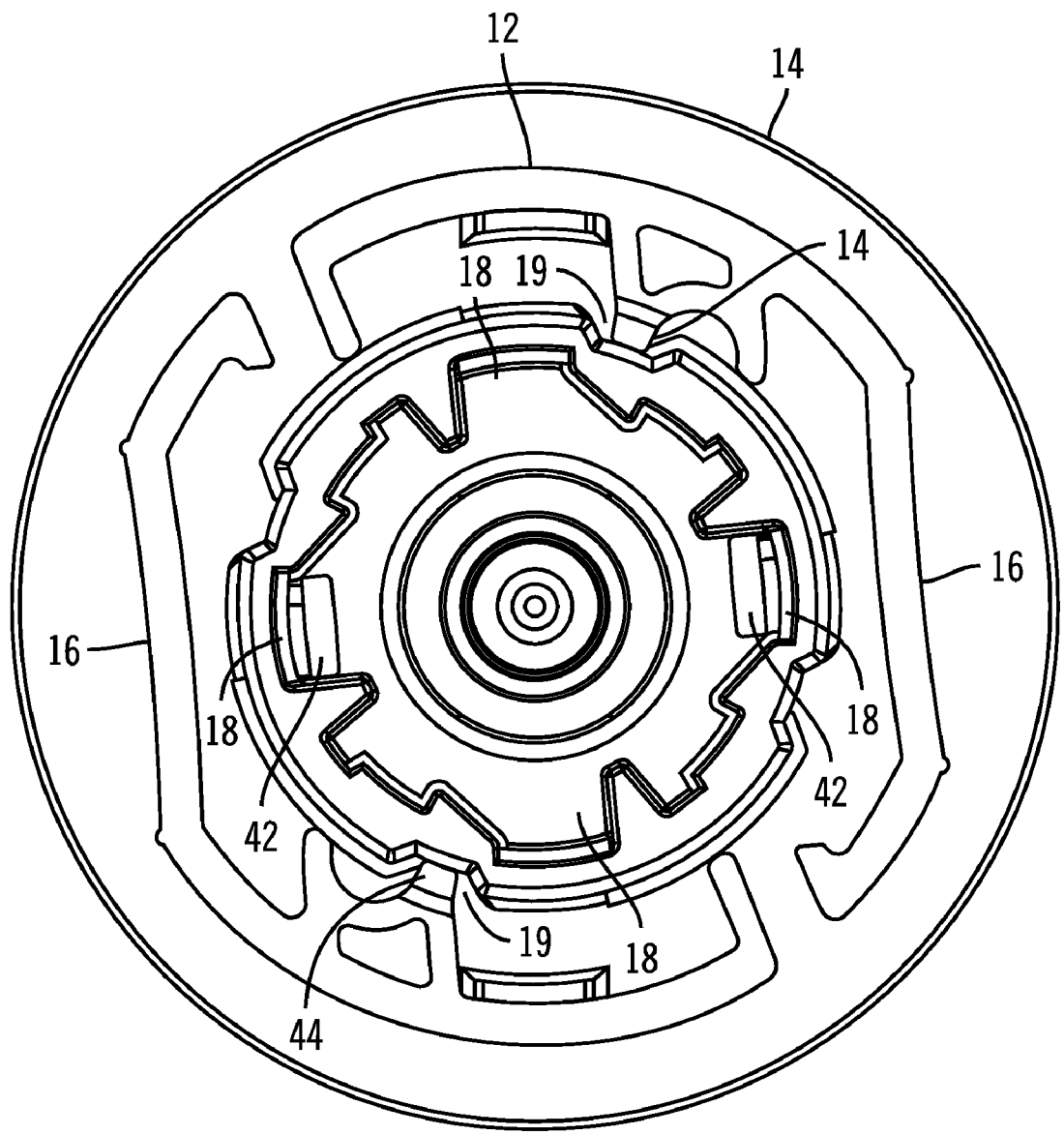
FIG. 6 shows a top-down, skeletal view of a connector as it engages a base in an unlocked position according to an embodiment of the present invention.

FIG. 6 shows a top down, skeletal view of the connector 12 as it engages the base 13 in an unlocked position according to an embodiment of the present invention. As can be seen in the embodiment of the invention shown in FIG. 6, the inner tabs 42 are positioned in the inner depressions 18. In the embodiment of the invention shown in FIG. 6, the connector 12 has two arms 16 and two inner tabs 42. However, the connector 12 may include more than two arms 16 and more than two inner tabs 42. In addition, the base 14 in the embodiment of the invention shown in FIG. 6 includes four inner depressions 18, despite the fact that the connector 12 includes only two inner tabs 42 in the embodiment of the invention shown in FIG. 6. The presence of a plurality of inner depressions 18 allows the connector 12 to engage the base 14 in a plurality of positions. Any number of inner depressions 18 may be configured in the base 14. For example, according to embodiments of the present invention, the base 14 may be configured with two, three, four, five, six or more depressions.

Also shown in the embodiment of the invention of FIG. 6 are outer tabs 44 and outer depressions 19. Much in the same way that the inner tabs 42 are positioned in the inner depressions 18 when the connector 12 engages the base 14, the outer tabs 44 are positioned in the outer depressions 19 when the connector 12 engages the base 14. Both the inner tabs 42 and the outer tabs 44 may be used to guide the connector 12 around the base 14 and to lock the connector 12 to the base 14 as will be explained in greater detail below.

Figure 7:
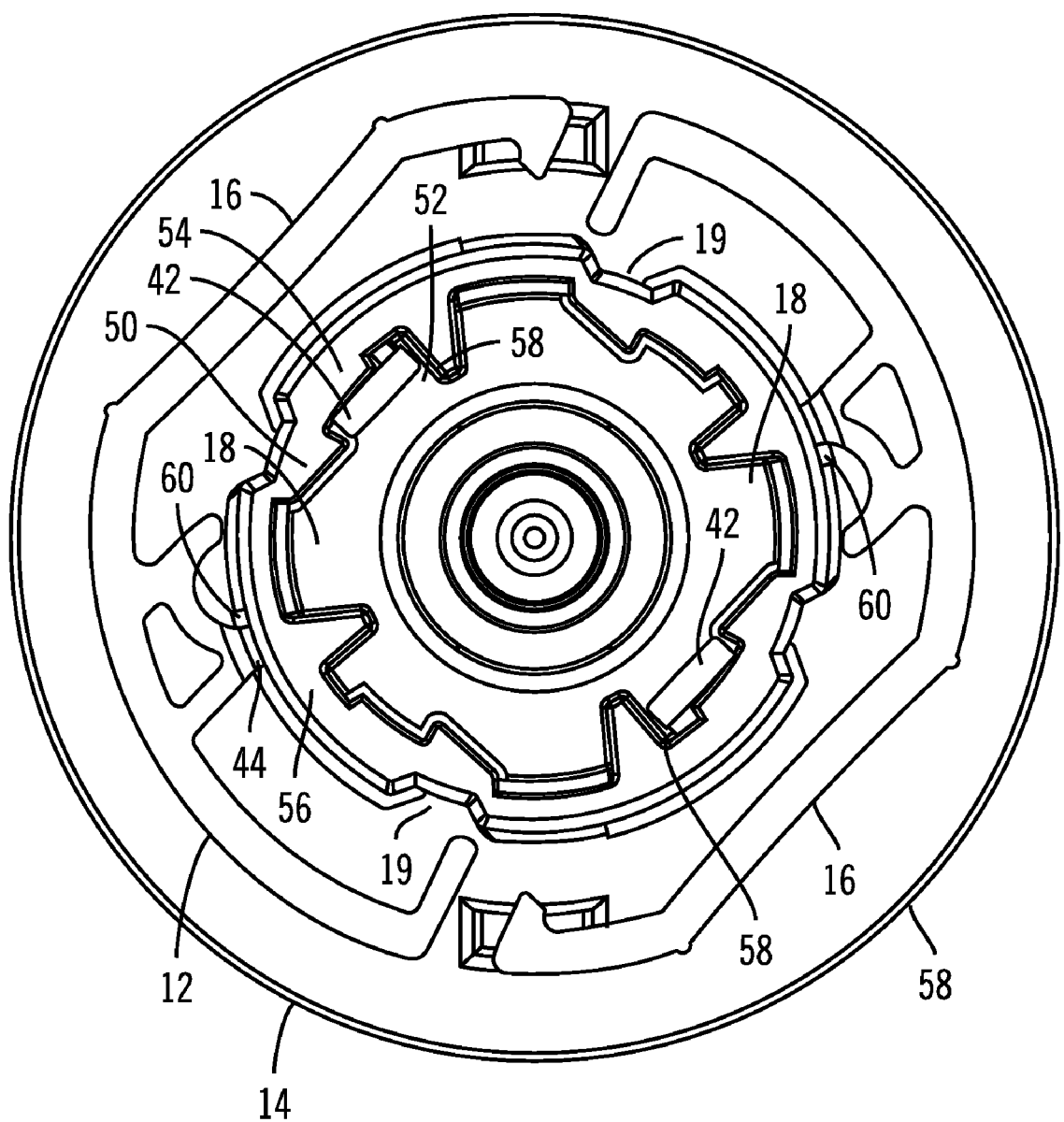
FIG. 7 shows a top-down, skeletal version of a connector as it engages a base in a locked position according to an embodiment of the present invention.

FIG. 7 shows a top down, skeletal version of the connector 12 engaged with the base 14 in a locked position according to an embodiment of the present invention. In the embodiment of the invention shown in FIG. 7, the connector 12 has been rotated from its unlocked position, and, thus, as can be seen in FIG. 7, the inner tabs 42 are no longer disposed in the inner depressions 18. Rather, as the connector 12 has been rotated about the base 13, the inner tab 42 travels radially along the cam 50 and is forced toward the center of the base 14 due to the flexibility of the arm 16. When the connector 12 has been rotated about the base 14 far enough so that the inner tab 42 of the connector 12 reaches the locking depression 52, the inner tab 42 "snaps" into the locking depression 52 of the base 14.

An inner underportion 54 is configured such that a portion of the inner tab 42 resides underneath the inner underportion 54, thereby preventing axial movement of the connector 12. The inner tab 42 of the connector 12 is prevented from additional rotation by an inner stop surface 58 and by a proximate end of the cam 50 of the base 14.

Also as the connector 12 is being rotated about the base 14, the outer tab 44 of the connector 12 moves radially along with the connector and is prevented from additional rotation by the second stop surface 60 of the base 14. An outer underportion 56 is configured such that a portion of the outer tab 44 resides underneath the outer underportion 56, thereby preventing axial movement of the connector 12 in the direction of the outer underportion 56 and providing a redundant function of preventing axial movement in addition to that afforded by positioning the inner tab 42 under the inner underportion 54.

Thus, as can be seen in FIG. 7, the connector 12 is in a locked position with respect to the base 14 in a number of respects. The inner tab 42 of the connector 12 is precluded from rotation relative to the base 14 when disposed in the locking depression 52 of the base 14 due to the barriers provided by the cam 50 and the first stop surface 58 of the base 14. Likewise, the outer tab 44 of the connector 12 is precluded from rotation (in the embodiment of the invention shown in FIG. 7, in the clockwise direction) by the second stop surface 60. Additionally, both the inner tab 42 and the outer tab 44 of the connector 12 are prevented from moving axially relative to the base 14 due to the underportions 54 and 56, respectively. Because a portion of the inner tab 42 and the outer tab 44 of the connector 12 reside under the inner underportion 54 and the outer underportion 56, respectively, of the base 14, in that state the connector 12 is effectively precluded from moving away from the base 14. Thus, depression of only one arm 16 is ineffective to remove the connector 12 from the base 14.

In order to remove the connector 12 from the base 14, both arms 16 of the connector 12 may be manually depressed, thereby positioning the inner tabs 42 of the connector 12 away from the locking depressions 52 of the base 14 and removing a portion of the inner tabs 42 from the inner underportions 54 of the base 14. Once the inner tabs 42 have been freed from the locking position due to depression of the arms 16, the connector 12 may be rotated in a direction opposite that used to place the connector 12 in a locking position (in the case of the embodiment of the invention shown in FIG. 7, in a counter-clockwise direction). In the embodiment of the invention shown in FIG. 7, both arms 16 must be depressed in order to free the inner tabs 42 of the connector 12 from the locking depressions 52 of the base 14. When, after rotation, the inner tabs 42 of the connector 12 reach the inner depression 18 of the base 14 and the outer tabs 44 of the connector 12 reach the outer depressions 19 of the base 14, the connector 12 may be removed from the base 14.

Figure 8:
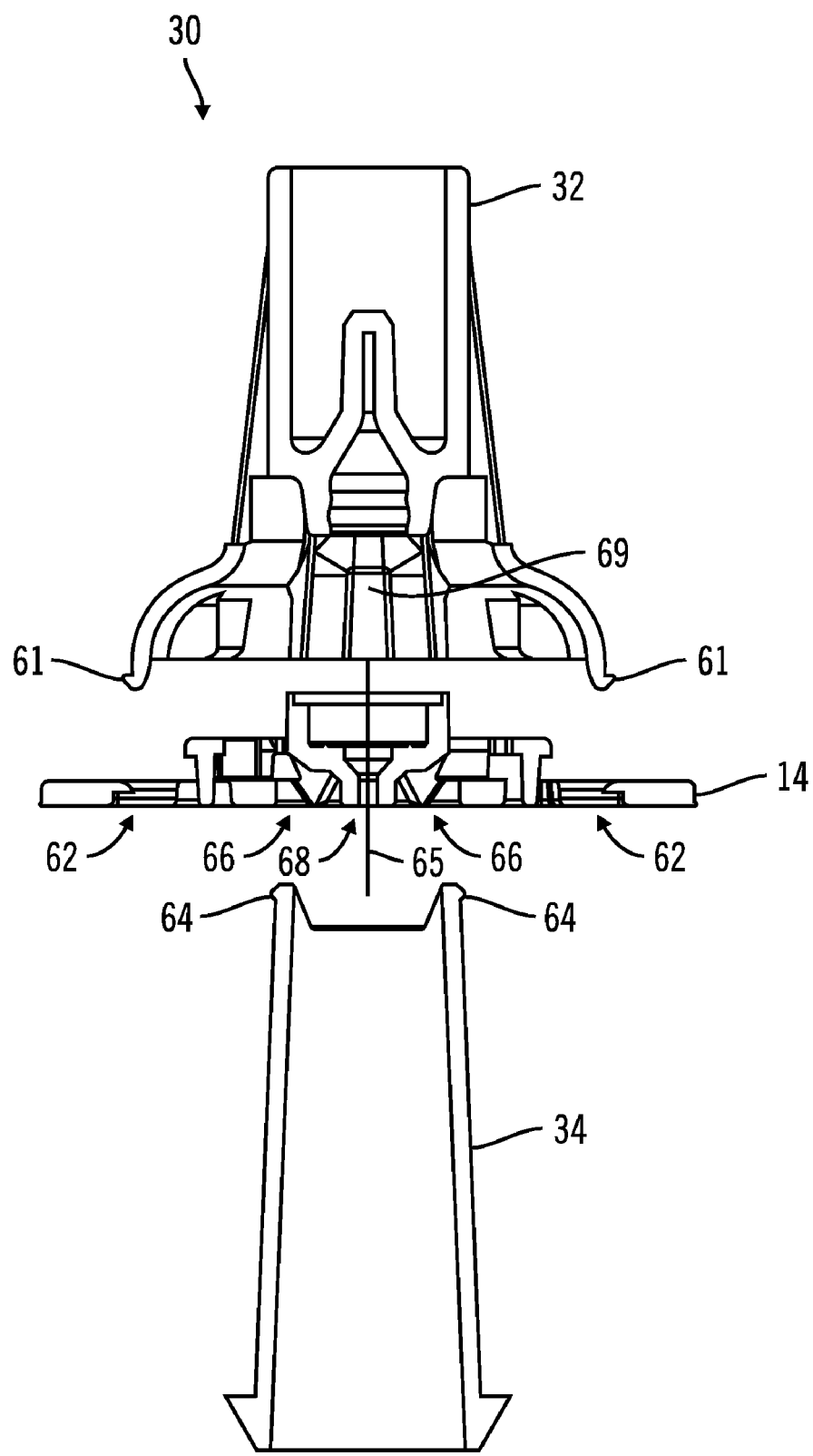
FIG. 8 shows an exploded, cutaway view of an infusion set according to an embodiment of the present invention.

FIG. 8 shows an exploded, cutaway view of the infusion set 30 according to an embodiment of the present invention. In the embodiment of the invention shown in FIG. 8, the hub 32 includes generally rigid hub tabs 61 that have enough flexibility to permit the hub 32 to be removably attached to the base 14 via base apertures 62. Similarly, the guard 34 includes generally rigid guard tabs 64 that have enough flexibility to permit the guard 34 to be removably attached to the base 14 via guard depressions 66. As can also be seen in FIG. 8, the hub 32 may include a hub chamber 69 in which a needle 65 may be affixed. The needle may extend through the base duct 68 and into and through a cannula (not shown) affixed to the base 14 at the opening of the base duct 68. The guard 34 may afford protection from the needle.

Figure 9:
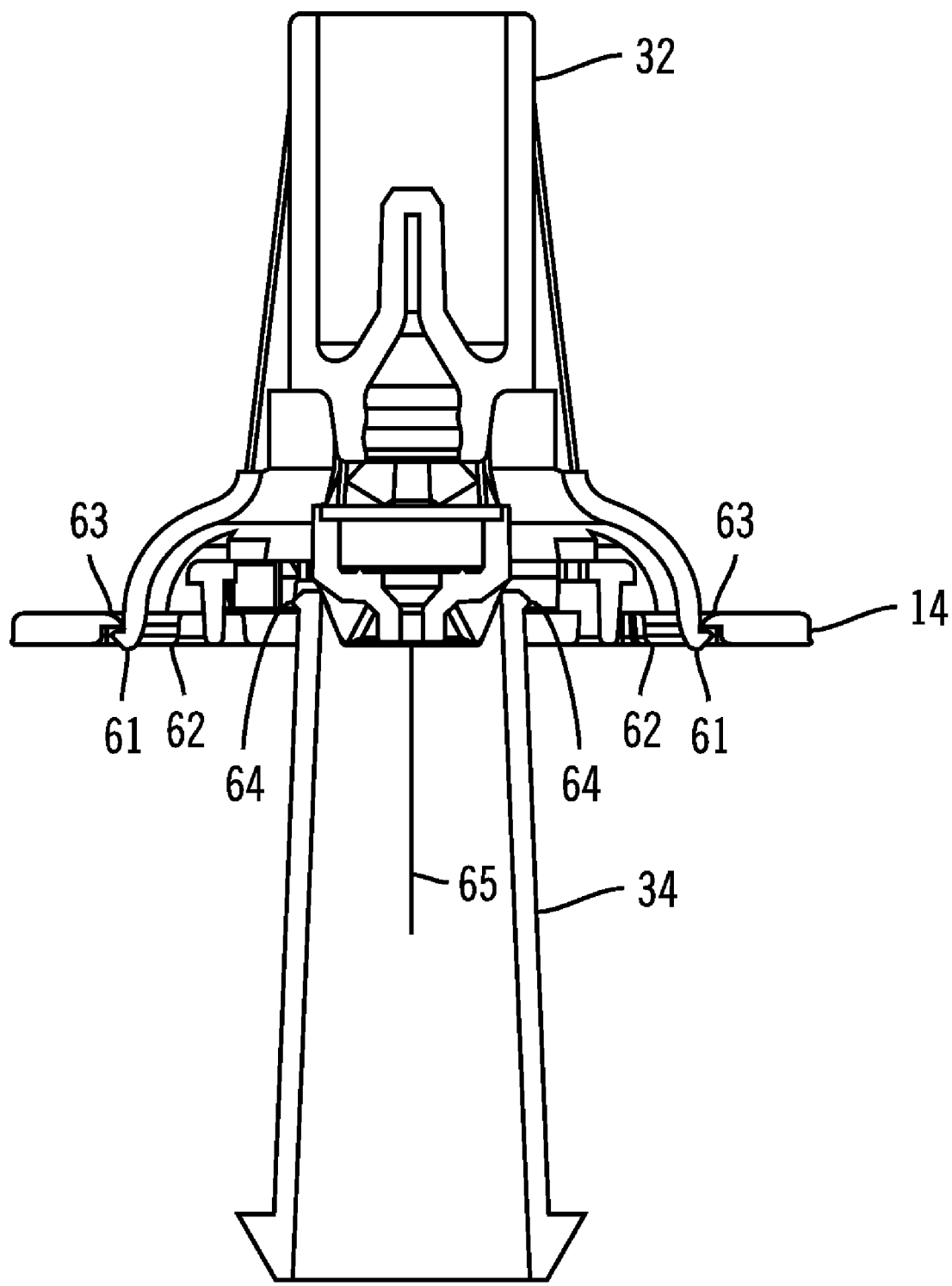
FIG. 9 shows a cutaway view of a hub and a guard removably attached to a base according to an embodiment of the present invention.

FIG. 9 shows a cutaway view of the hub 32 and guard 34 removably attached to the base 14 according to an embodiment of the present invention. As stated previously, this configuration may be used for storage of the device until a patient is ready to affix the base 14 to the patient's skin. It can be seen in FIG. 9 that the hub tabs 61 have been inserted into the base apertures 62 and are maintained in their position via lips 63 that extend into the base apertures 62. Likewise, the guard tabs 64 have been extended into the guard depressions 66 in the base 14. Both the hub 32 and the guard 34 may be removed from the base 14 by squeezing the body of the hub 32 and the guard 34 in an area close to their respective tabs and separating the hub 32 and the guard 34 from the base 14.

The hub 32 and the guard 34 may also be used together after a patient has positioned the base 14 onto his or her skin. For example, a patient may insert a cannula attached to the base 14 subcutaneously by removing the guard 34 and pushing the needle 65 and cannula into the skin by forcing the hub 32 and the base 14 onto the skin surface while the hub 32 remains affixed to the base 14. However, after subcutaneous insertion of the cannula, the hub 32 may be removed from the base 14, thereby exposing the needle 65 attached to the hub 32. By including apertures (not shown) on the hub 32 configured to accept the guard tabs 64, the guard 34 may be positioned over the needle 65 attached to the hub 32 to protect the patient or anyone else from the needle 65 until the hub 32 can be disposed.

Figure 10:
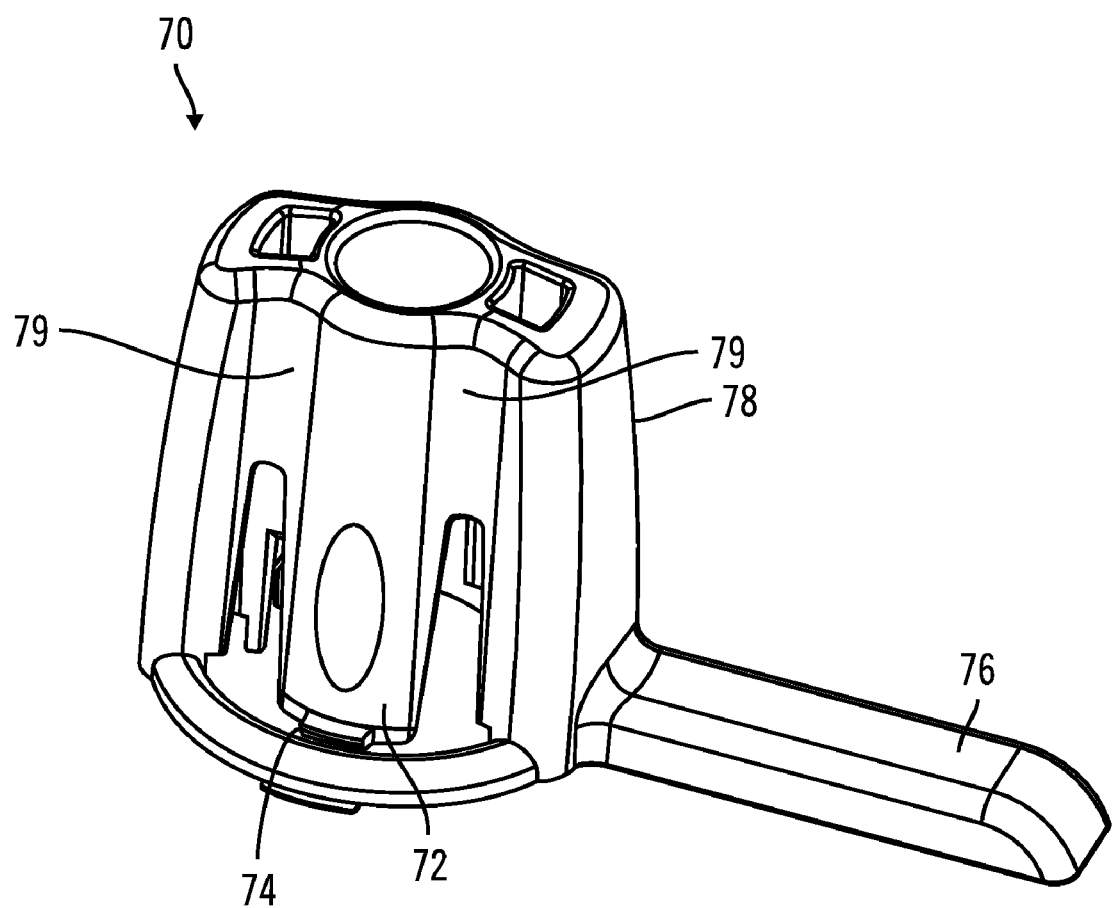
FIG. 10 shows another embodiment of a hub according to an embodiment of the present invention.

FIG. 10 shows another embodiment of a hub 70 according to an embodiment of the present invention. The embodiment of the hub 70 shown in FIG. 10, includes, without limitation, a hub arm 72, a hub tab 74, a hub extension 76 and hub body 78. In FIG. 10, the hub arm 72 has been configured for flexibility, providing adequate movement of the hub tab 74 and allowing for relatively easy application and removal of the hub 70 to a base, such as base 14 described above. In addition, one or more hub tabs 74 may be positioned at the end of a hub arm 72 to lock the hub 70 to a base. The hub extension 76 may be designed with sufficient length to allow a user to hold onto the hub 70 with one hand when using the other hand to remove an insertion tool that may be used with the device or as an aid in positioning the device onto the skin. The hub body 78 may be designed of sufficient size and geometry to allow a user to readily grip and hold onto it, for example, as between a thumb and a forefinger. For example, in the embodiment of the invention shown in FIG. 10, the hub body 78 includes grooves 79 that provide additional friction to a user when holding onto the hub 70.

Figure 11:
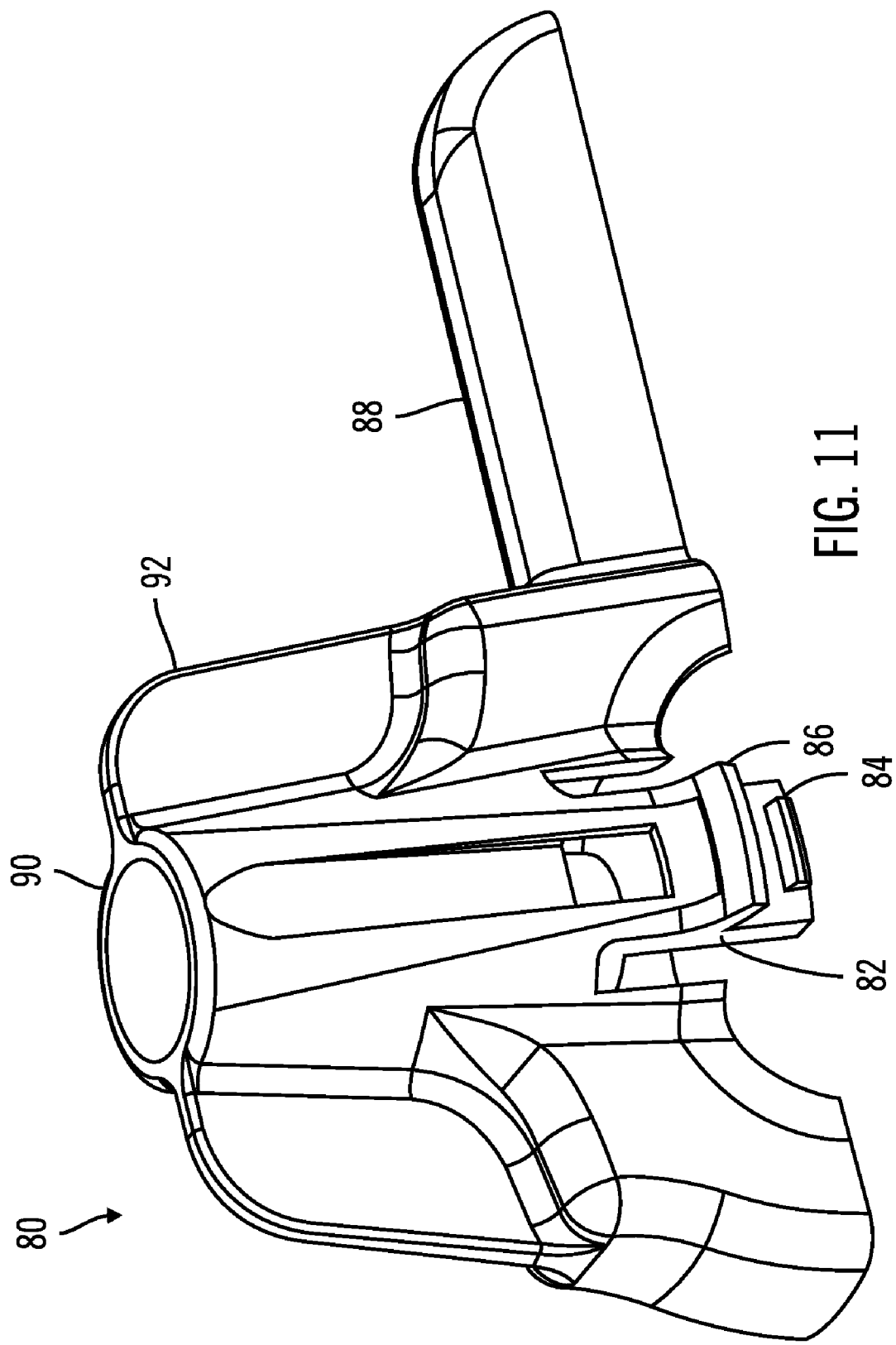
FIG. 11 shows another embodiment of a hub according to an embodiment of the present invention.

FIG. 11 shows another embodiment of a hub 80 according to an embodiment of the present invention. In the embodiment of the invention shown in FIG. 11, the hub 80 includes, without limitation, a hub arm 82, a hub extension 88 and a hub body 90. The hub arm 82 may include one or more hub tabs 84 and a wing 86. The hub tab 84 may be used to lock the hub 80 into a base, such as base 14 described above. The wing 86 may be used to provide additional leverage for a user when inserting the hub 80 onto a base or removing the hub 80 from a base. As can be seen in FIG. 11, the hub arm 82 has been designed to be flexible to allow a user to perform these operations. The hub extension 88 may be designed with sufficient length to allow a user to hold onto the hub 80 when positioning the hub 80 in a base onto the user's skin, for example, with an insertion tool. The hub body 90 may be designed with sufficient size and geometry to allow a user to readily grip and hold onto the hub 80. For example, in the embodiment of the invention shown in FIG. 11, the hub body 90 includes hub flanges 92 with which a user may grab the hub 80, such as, for example, between a thumb and a forefinger.

Figure 12:
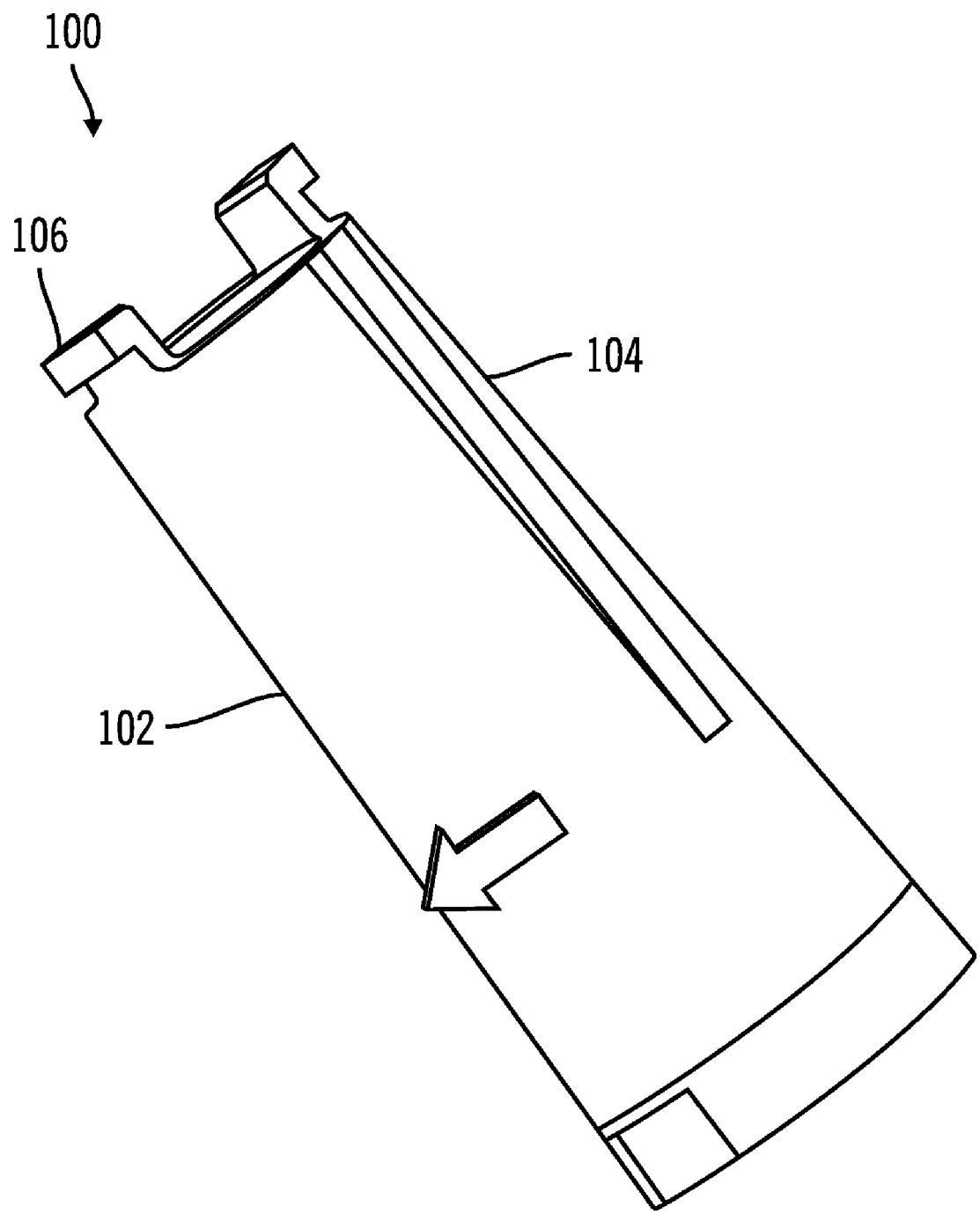
FIG. 12 shows an embodiment of a guard according to an embodiment of the present invention.

FIG. 12 shows an embodiment of a guard 100 according to an embodiment of the present invention. In the embodiment of the invention shown in FIG. 12, the guard 100 may include, without limitation, a body 102, one or more slots 104 and one or more tabs 106. The body 102 may be designed with sufficient size and geometry to enclose a needle or other protrusion which may be extending away from a base or other part of the device. For example, in the embodiment of the invention shown in FIG. 12, the body 102 is substantially cylindrical and has a slight taper. Generally rigid tabs 106 at one end of the body 102 have sufficient flexibility to allow the guard 100 to be removably affixed onto a base or hub as the case may be. The slot 104 facilitates manual "squeezing" of the body 102, thereby making it easier for a user to insert or remove the tabs 106 from a body or a hub.

Figure 13:
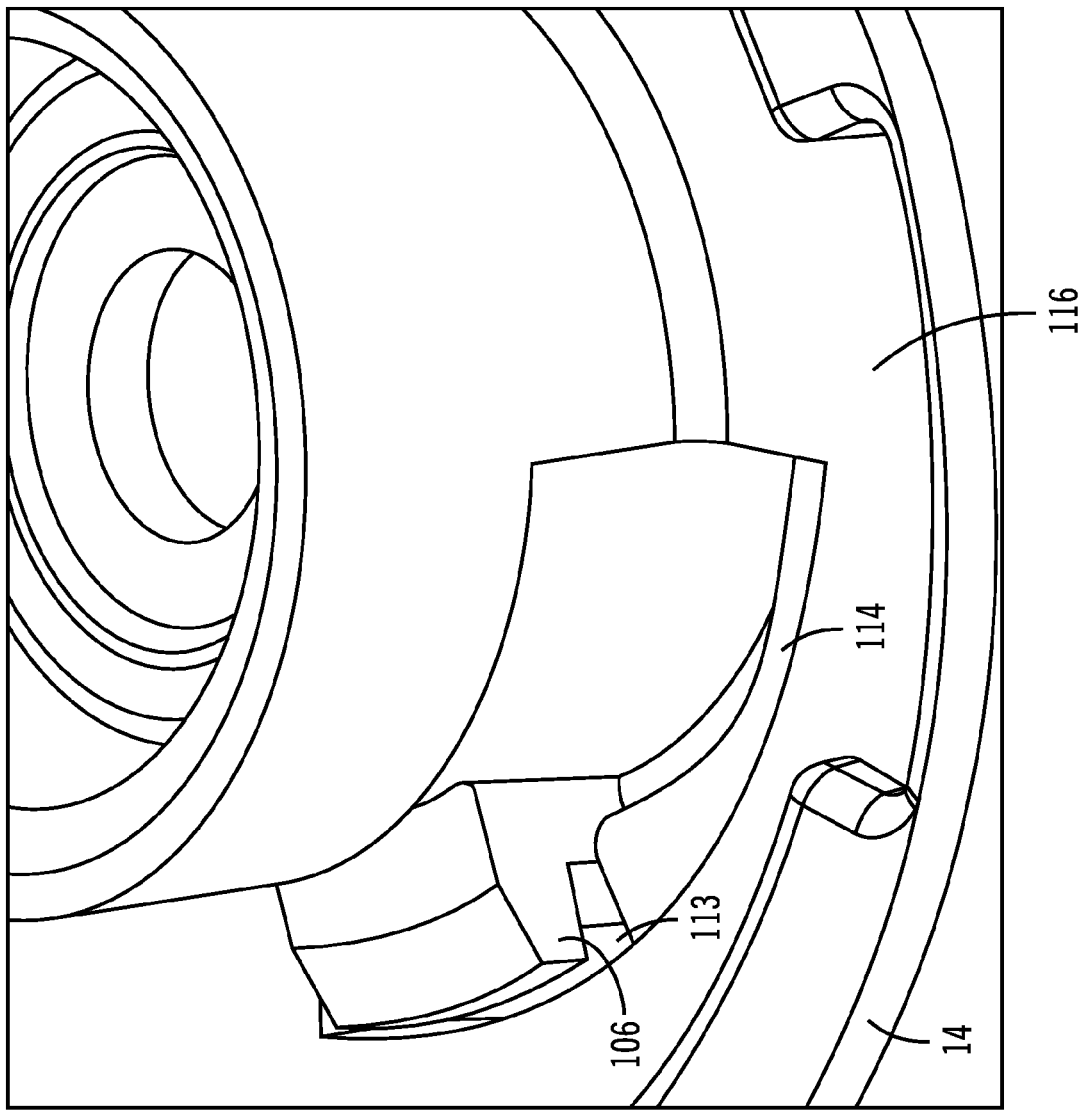
FIG. 13 shows an embodiment of a guard tab interfacing with a base in an unlocked position according to an embodiment of the present invention.

FIG. 13 shows an embodiment of a guard tab 106 interfacing with a base 14 in an unlocked position according to an embodiment of the present invention. In the embodiment of the invention shown in FIG. 13, a guard tab 106 has been inserted into a tab opening 113 on the base 14. The tab opening 113 has been designed for easy insertion of the guard tab 106. The base 14 also includes an underportion 114 which, when the guard tab 106 is rotated away from the tab opening 113, will be positioned underneath a portion of the guard tab 106 and will prevent the guard from being removed from the base.

Figure 14:
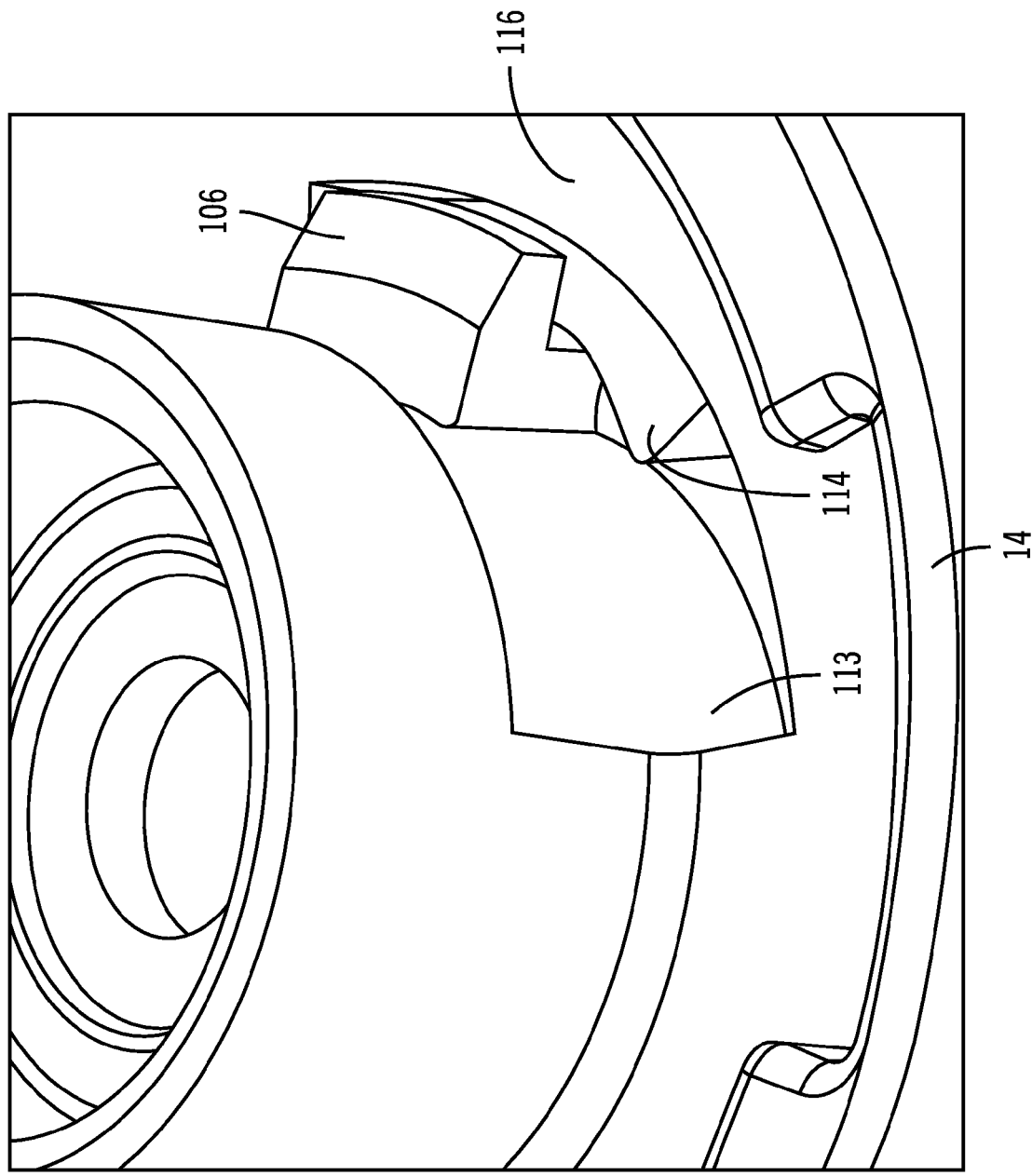
FIG. 14 shows an embodiment of a guard tab interfacing with a base in a locked position according to an embodiment of the present invention.

FIG. 14 shows the guard tab 106 of FIG. 13 in a locked position according to an embodiment of the present invention. In FIG. 14, the guard tab 106 has been rotated over the underportion 114 in the base 14 such that a face of the guard tab 106 engages an edge of the underportion 114. This configuration is possible because the surface of the underportion 114 in the base 14 is lower than the base surface 116. To remove the guard from the base 14 in this embodiment, the guard tab 106 may be rotated toward the tab opening 113, away from the underportion 114 so that a user may pull the guard away from the base 14.

Figure 15:
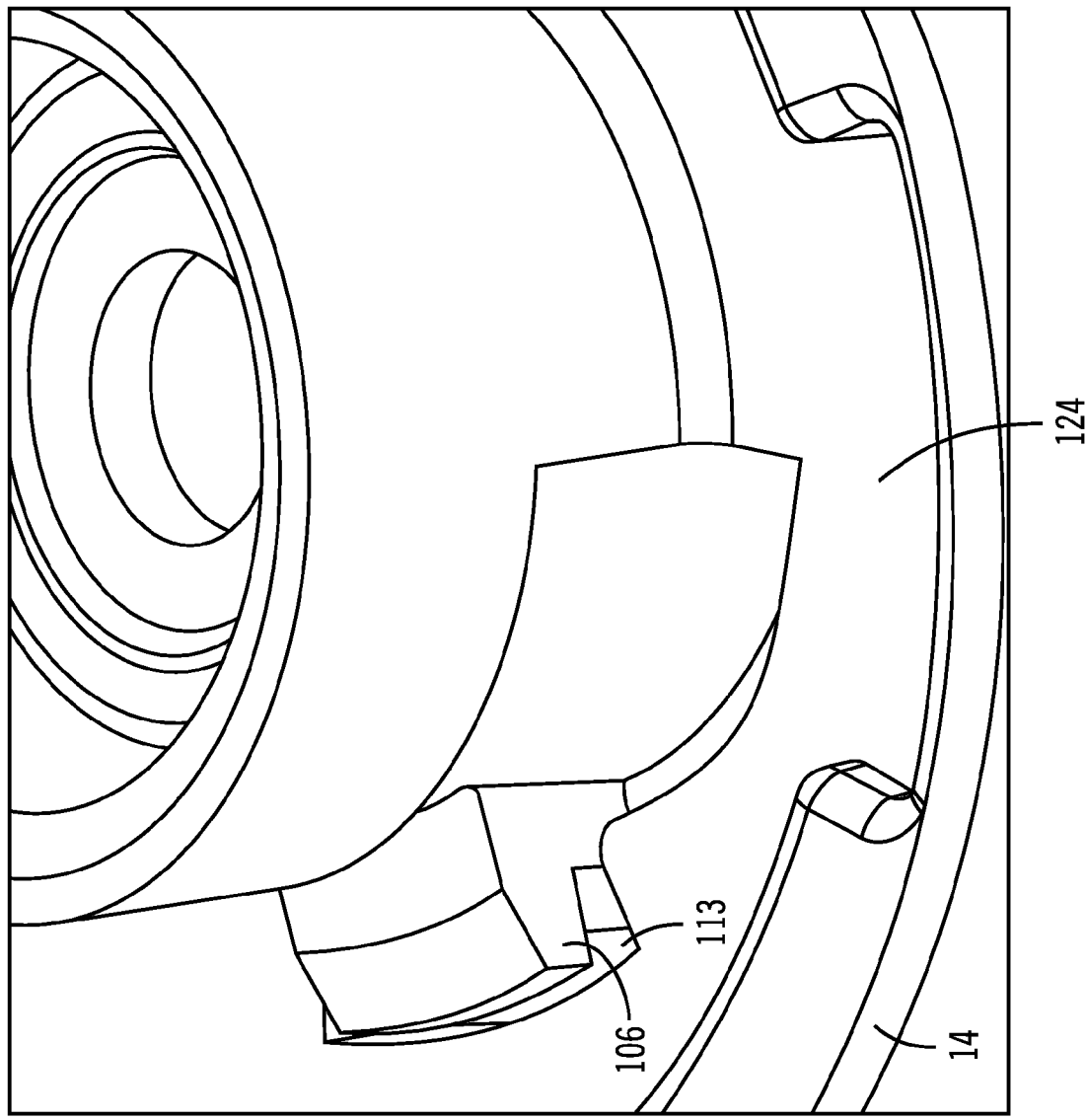
FIG. 15 shows another embodiment of a guard tab interfacing with a base in an unlocked position according to an embodiment of the present invention.
Figure 16:
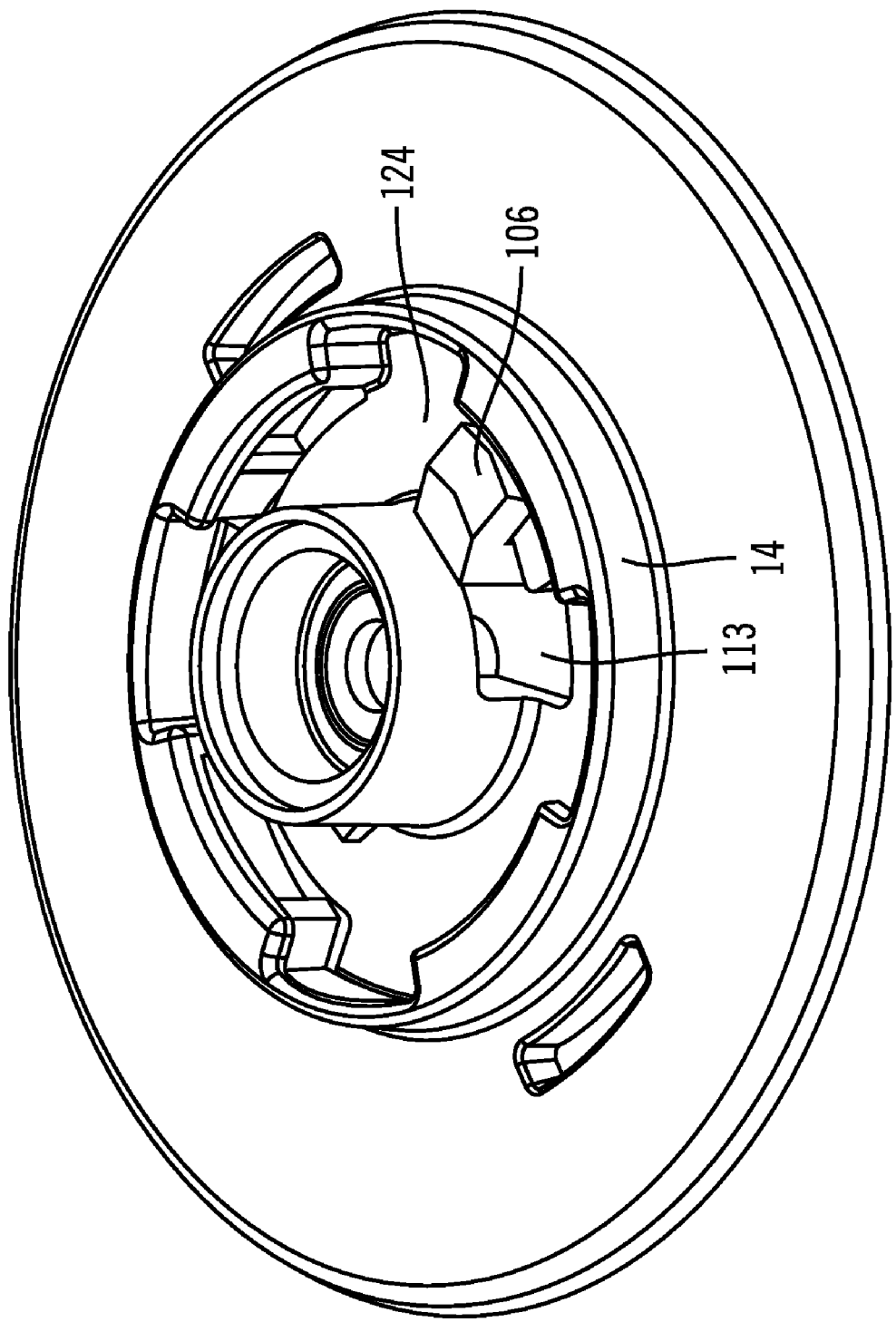
FIG. 16 shows another embodiment of a guard tab interfacing with a base in a locked position according to an embodiment of the present invention.

FIG. 15 shows a guard tab engaging a base according to an embodiment of the present invention. In FIG. 15, the guard tab 106 is positioned in the tab opening 113 of the base 14. In FIG. 15, the guard tab 106 is in an unlocked position in the base 14. In FIG. 16, the guard tab 106 has been rotated about the base surface 124 so that the face of the guard tab 106 rests on an edge of the base surface 124. In this position, the guard tab 106 is locked into the base 14. In the embodiment of the invention shown in FIG. 15 and FIG. 16, the base 14 does not include an underportion and, consequently, the base 14 serves as the mechanism preventing the guard tab 106 from being removed from the base 14.

Figure 17:
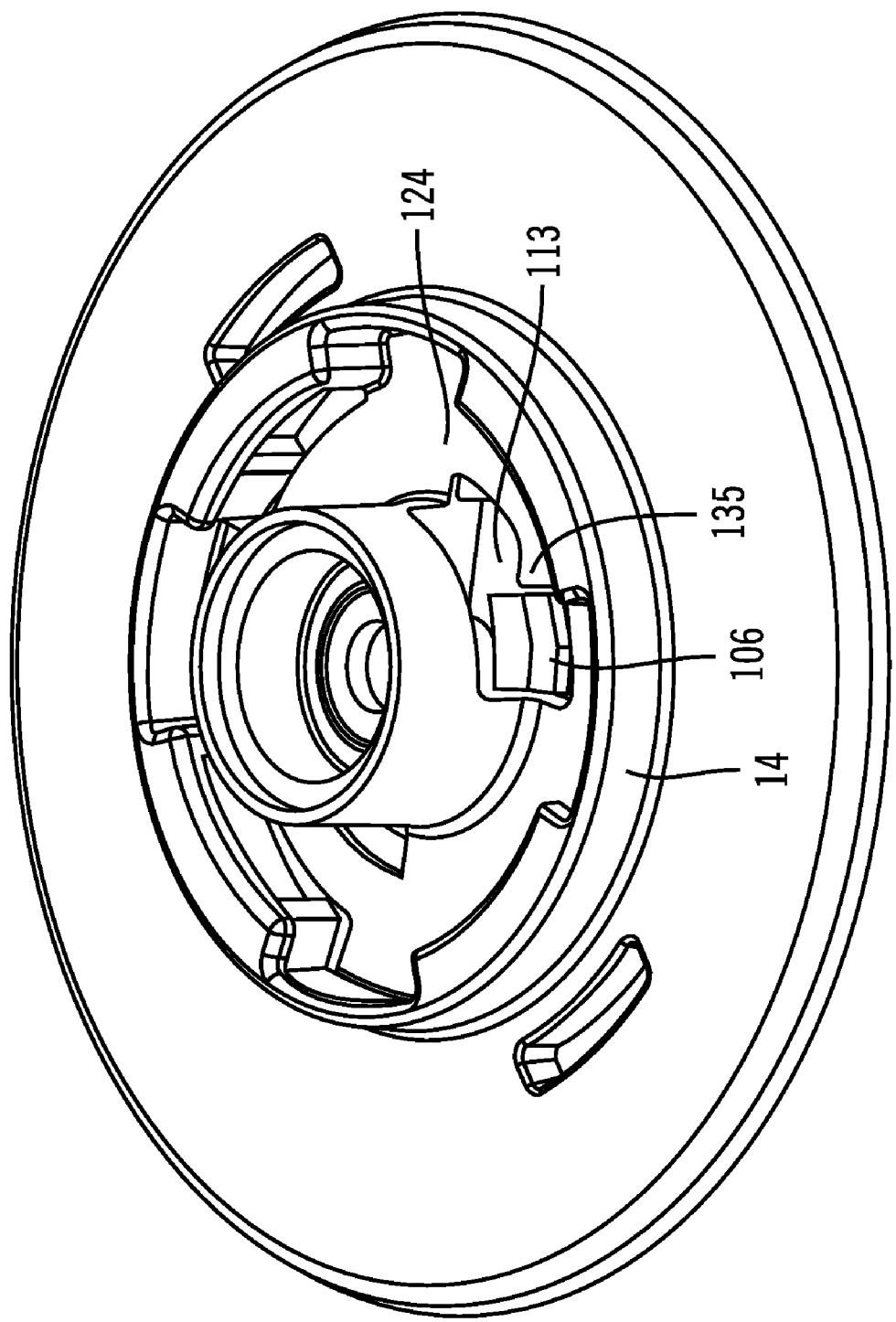
FIG. 17 shows another embodiment of a guard tab interfacing with a base in an unlocked position according to an embodiment of the present invention.
Figure 18:
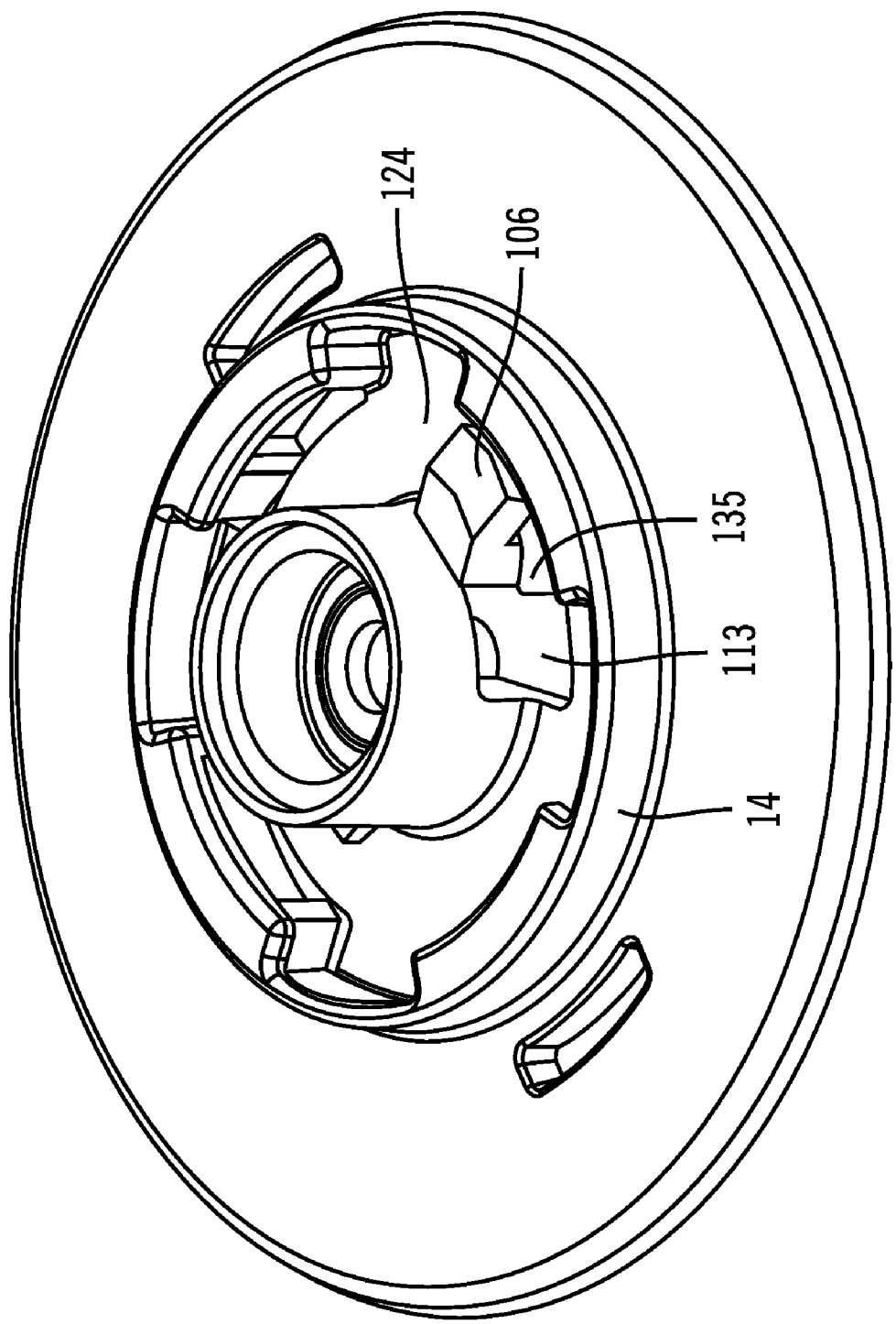
FIG. 18 shows another embodiment of a guard tab interfacing with a base in a locked position according to an embodiment of the present invention.

FIGS. 17 and 18 show a guard tab 106 in locked and unlocked positions, respectively, on a base 14. The guard tab 106 may be rotated from the guard depression 133 so that a face of the guard tab 106 rests on an edge of the base surface 124. In the embodiment of the invention shown in FIGS. 17 and 18, a protrusion 135 on the base surface 124 extends away from the base surface 124 into the space through which the guard tab 106 rotates, requiring an additional active movement by the user, such as, for example, a manual "squeezing" of the guard to move the guard tab 132 from a locked position to an unlocked position and vice versa.

Figure 19:
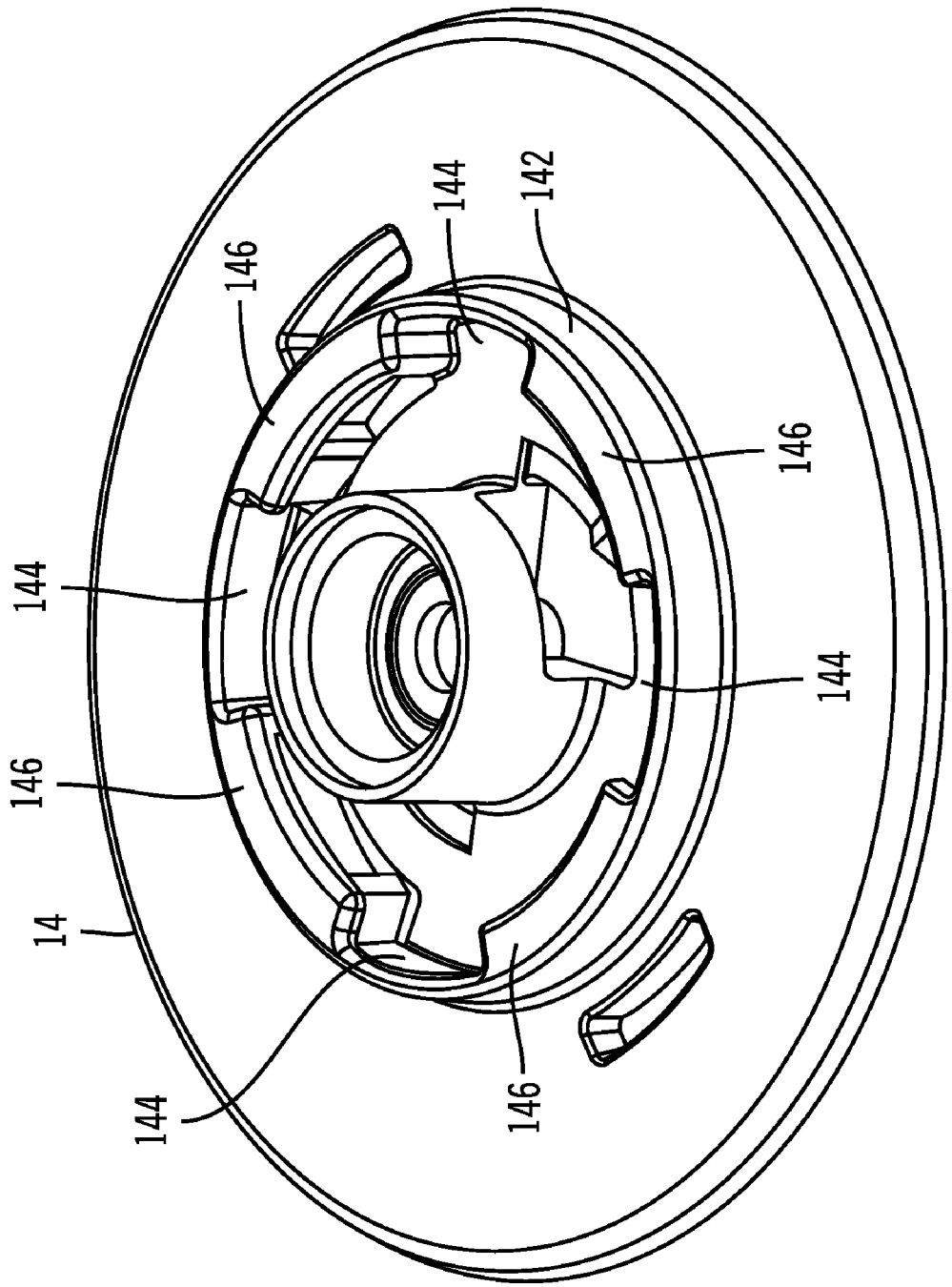
FIG. 19 shows perspective view of another base according to an embodiment of the present invention.

FIG. 19 shows a base 14 according to an embodiment of the present invention. In FIG. 19, the base 14 includes, without limitation, a rim 142, the outside of which is substantially smooth. The rim 142 shown in FIG. 19 is advantageous in that, when the base 14 is positioned on a user's or patient's skin, the smooth outside portion of the rim 142 may minimize the snagging or catching of clothing and the like.

Figure 20:
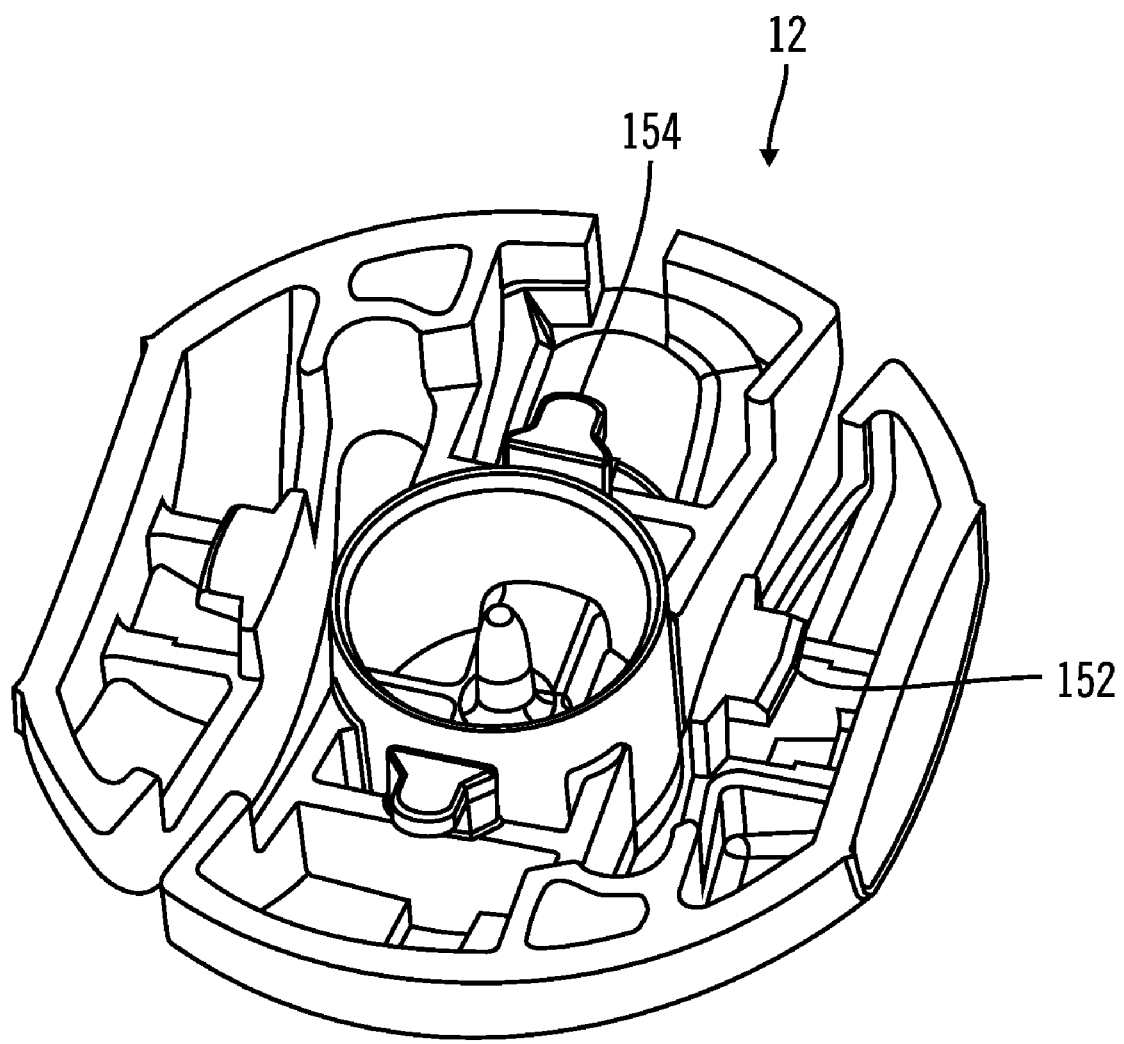
FIG. 20 shows a perspective view of another connector according to an embodiment of the present invention.

FIG. 20 shows a connector 12 suitable for use with a base such as the base 14 shown in FIG. 19 according to an embodiment of the present invention. In FIG. 20, the connector 12 includes flexible tabs 152 and static tabs 154, all of which may be insertable into depressions 144 of the base 14 shown in FIG. 19. Thus, the connector 12 may be positioned onto the base 14 in a plurality of orientations, but, when the connector 12 is rotated such that the flexible tabs 152 and the static tabs 154 are positioned under base edges 146 of the base 14, the connector 12 will be locked onto the base 14.

The flexible tabs 152 and the static tabs 154 may be designed in a variety of ways. For example, in the embodiment of the invention shown in FIG. 20, the flexible tabs 152 have been designed with corners to facilitate locking of the flexible tabs 152 with the base edges 146. However, because the flexible tabs 152 are moveable due to their attachment to the arms of the connector, insertion and removal of the flexible tabs 152 from the base edges 146 is still possible via a positive action by the user. The static tabs 154, on the other hand, are generally not moveable by a user in the embodiment of the invention shown in FIG. 20 and, thus, have been designed with more rounded features to ease engagement with the base edges 146.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. An infusion set comprising:
   a base removably attachable to an infusion site for providing a subcutaneous path for an infusant, the base having a cannula;
   a hub removably attachable to the base, the hub including a needle for extending through the base and through the cannula; and
   a guard removably attachable to the hub for surrounding the needle when the guard is attached to the hub;
   wherein, upon removal of the guard, the needle is subcutaneously insertable into the infusion site for subcutaneously positioning the cannula;
   wherein the guard engages the hub when the guard is attached to the hub and is surrounding the needle.

2. An infusion set as recited in claim 1, the base having at least one aperture and the guard having at least one extended portion for extending into the at least one aperture of the base.

3. An infusion set as recited in claim 1, wherein the guard is removably attachable to the base to cover the needle when the hub is attached to the base and the needle is extended through the base and cannula.

4. An infusion set as recited in claim 1, wherein the guard attaches to the hub via a locking mechanism.

5. An infusion set as recited in claim 1, wherein the guard and the base have at least one aperture and at least one extending portion for removably attaching the guard to the base; and the at least one extending portion of the guard engages the hub.

6. An infusion set as recited in claim 1, wherein the guard and the base have a plurality of apertures and a corresponding plurality of extending portions for removably attaching the guard to the base.

7. An infusion set as recited in claim 1, wherein the guard and the hub have a plurality of apertures and a corresponding plurality of extending portions for attaching the guard to the hub.

8. An infusion set as recited in claim 1, wherein the guard has at least one portion for extending through an aperture in the base to removably attach the guard to the base, the at least one portion of the guard also for engaging the hub to attach the guard to the hub wherein the guard covers the needle when the guard is attached to the hub.

9. An infusion set as recited in claim 1, wherein the guard has a plurality of portions for extending through a corresponding plurality of apertures in the base to removably attach the guard to the base, the plurality of portions of the guard also for engaging the hub to attach the guard to the hub, wherein the guard covers the needle when the guard is attached to the hub.

10. An infusion set as recited in claim 1, wherein:
the base has a plurality of apertures and the guard has a plurality of tabs for engaging the plurality of apertures of the base for releasably connecting the guard to the base;
the base has a plurality of locking surfaces;
wherein the guard is at least partially rotatable about an axis of the base; and
wherein rotation of the guard about the base causes the plurality of tabs to engage with the plurality of locking surfaces to inhibit separation of the guard from the base in an axial direction parallel to the axis of the base.

11. An infusion set comprising:
a base removably attachable to an infusion site for providing a subcutaneous path for an infusant, the base having a cannula;
a hub removably attachable to the base, the hub including a needle for extending through the base and through the cannula; and
a guard removably attachable to the base opposite the hub for surrounding the needle, the guard and the base having at least one aperture and locking surface and at least one tab for engaging the at least one aperture, for releasably attaching the guard to the base;
wherein the guard is at least partially rotatable about an axis of the base;
wherein rotation of the guard about the base causes the tab to engage with the locking surface to inhibit separation of the guard from the base in an axial direction parallel to the axis of the base; and
wherein, upon removal of the guard, the needle is subcutaneously insertable into the infusion site for subcutaneously positioning the cannula.

12. An infusion set as recited in claim 11, the base having a plurality of apertures and the guard having a plurality of tabs for engaging the plurality of apertures of the base for releasably connecting the guard to the base.

13. An infusion set as recited in claim 12, the base having a plurality of locking surfaces for retaining the a plurality of tabs in the a plurality of apertures to inhibit separation of the base and the guard.

14. An infusion set as recited in claim 12,
wherein the guard has a body that is flexible; and
wherein the body of the guard has an outer surface arranged to be manually squeezed to cause the body of the guard to be flexed to remove the guard from the base.

15. An infusion set as recited in claim 11, wherein the hub has a flexible body capable of being manually squeezed to remove the hub from the base when the hub is attached to the base; and
wherein the base and the hub have at least one aperture and at least one tab for engaging the at least one aperture for releasably connecting the hub to the base.

16. An infusion set as recited in claim 15, the body of the hub having one or more flexible arms, each tab extending from a respective one of the one or more flexible arms.

17. An infusion set as recited in claim 15, the body of the hub having at least one wing for providing leverage to manually squeeze the body of the hub during insertion or removal of the at least one tab from the at least one aperture.

18. An infusion set as recited in claim 11,
wherein the hub has a body that is flexible; and
wherein the body of the hub has an outer surface arranged to be manually squeezed to cause the body of the hub to be flexed to remove the hub from the base.

19. An infusion set as recited in claim 11, the base removably lockable to a connector for providing a fluid flow path for the infusant to the subcutaneous path.

20. An infusion set comprising:
a base removably attachable to an infusion site for providing a subcutaneous path for an infusant, the base having a cannula;
a hub removably attachable to the base, the hub including a needle for extending through the base and through the cannula; and
a guard removably attachable to the base opposite the hub for surrounding the needle, the guard and the base having at least one aperture and at least one tab for engaging the at least one aperture, for releasably attaching the guard to the base, the guard having a flexible body capable of being manually squeezed to release and remove the guard from the base when the guard is attached to the base;
wherein, upon removal of the guard, the needle is subcutaneously insertable into the infusion site for subcutaneously positioning the cannula;
the base having a plurality of apertures and the guard having a plurality of tabs for engaging the plurality of apertures of the base for releasably connecting the guard to the base;
the base having a plurality of locking surfaces;
wherein the guard is at least partially rotatable about an axis of the base; and
wherein rotation of the guard about the base causes the plurality of tabs to engage with the plurality of locking surfaces to inhibit separation of the guard from the base in an axial direction parallel to the axis of the base.

* * * * *